(12) United States Patent
Jones et al.

(10) Patent No.: US 11,376,199 B2
(45) Date of Patent: *Jul. 5, 2022

(54) ANHYDROUS COSMETIC COMPOSITIONS AND USES

(71) Applicant: The Procter & Gamble Company, Cincinnati, OH (US)

(72) Inventors: Stevan David Jones, Hyde Park, OH (US); Dean Zimmerman, Cincinnati, OH (US); Mahmoud Eljack, Cincinnati, OH (US); Jorge Max Sunkel, West Chester, OH (US); William Richard Mueller, Cincinnati, OH (US); Scott Vierling, Cincinnati, OH (US); Steven Robert Sealschott, Cincinnati, OH (US); Larry Wayne Marshall, Liberty Township, OH (US); Timothy Roy Nijakowski, Mason, OH (US); Carl Edward Catrenich, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 82 days.

This patent is subject to a terminal disclaimer.

(21) Appl. No.: 16/813,771

(22) Filed: Mar. 10, 2020

(65) Prior Publication Data

US 2020/0289386 A1    Sep. 17, 2020

Related U.S. Application Data

(60) Provisional application No. 62/817,090, filed on Mar. 12, 2019.

(51) Int. Cl.
*A61K 8/27* (2006.01)
*A61K 8/73* (2006.01)
*A61K 8/81* (2006.01)
*A61K 8/60* (2006.01)
*A61K 8/362* (2006.01)
*A61Q 15/00* (2006.01)
*A61K 8/31* (2006.01)
*A61K 8/34* (2006.01)
*A61K 8/41* (2006.01)
*A61K 8/891* (2006.01)
*A61K 8/92* (2006.01)
*A61K 8/25* (2006.01)

(52) U.S. Cl.
CPC .............. *A61K 8/27* (2013.01); *A61K 8/25* (2013.01); *A61K 8/31* (2013.01); *A61K 8/342* (2013.01); *A61K 8/362* (2013.01); *A61K 8/416* (2013.01); *A61K 8/60* (2013.01); *A61K 8/731* (2013.01); *A61K 8/732* (2013.01); *A61K 8/736* (2013.01); *A61K 8/8147* (2013.01); *A61K 8/891* (2013.01); *A61K 8/92* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 4,675,178 A | 6/1987 | Klein | |
| 4,743,440 A | 5/1988 | Callingham et al. | |
| 6,004,584 A | 12/1999 | Peterson et al. | |
| 6,805,855 B2 | 10/2004 | Mattai | |
| 6,887,859 B2 | 5/2005 | Clapp | |
| 9,504,587 B2 | 11/2016 | Ta | |
| 9,943,844 B2 | 4/2018 | Baltenneck | |
| 10,543,164 B2 | 1/2020 | Sturgis | |
| 10,555,884 B2 | 2/2020 | Sturgis | |
| 2005/0191257 A1 | 9/2005 | Brahms | |
| 2008/0247978 A1 | 10/2008 | Mattai | |
| 2009/0151087 A1 | 6/2009 | Mario | |
| 2009/0282659 A1 | 11/2009 | Kato | |
| 2010/0119461 A1 | 5/2010 | Bicard-benhamou et al. | |
| 2010/0297201 A1 | 11/2010 | Gillece et al. | |
| 2014/0242015 A1* | 8/2014 | Fares | A61K 8/19 424/67 |
| 2016/0271045 A1 | 9/2016 | Berry et al. | |
| 2016/0374933 A1 | 12/2016 | Tanner | |
| 2017/0216182 A1 | 8/2017 | Banowski | |
| 2018/0168947 A1 | 6/2018 | Banowski | |
| 2018/0168985 A1 | 6/2018 | Banowski | |
| 2019/0000734 A1 | 1/2019 | Sturgis | |

(Continued)

FOREIGN PATENT DOCUMENTS

| | | |
|---|---|---|
| CN | 102840910 A | 8/2012 |
| CN | 107285946 A | 10/2017 |

(Continued)

OTHER PUBLICATIONS

All Office Actions; U.S. Appl. No. 16/813,769.
All Office Actions; U.S. Appl. No. 16/813,770.
Database WPI Week 201310 Thomson Scientific, London, GB; AN 2012-Q23352, XP002791211.
Database WPI Week 201779 Thomson Scientific, London, GB; AN 2017-753300 ,XP002791210.

(Continued)

*Primary Examiner* — Melissa L Fisher
(74) *Attorney, Agent, or Firm* — Kathleen Y Carter

(57) ABSTRACT

Described herein, an anhydrous cosmetic composition includes one or more water-absorbing components; a malodour-controlling component; a cosmetically acceptable carrier; wherein the anhydrous cosmetic composition has a burst resistance pressure greater than about 137.9 mBar (2 psi); wherein the anhydrous cosmetic composition has a water vapor sorption per 100 g of the composition from about 2.0 g to about 15 g; and wherein the anhydrous cosmetic composition is essentially free of aluminium-based antiperspirant actives.

7 Claims, 3 Drawing Sheets

(56) References Cited

U.S. PATENT DOCUMENTS

| | | | |
|---|---|---|---|
| 2019/0224102 A1* | 7/2019 | Banowski | A61K 8/342 |
| 2019/0358134 A1 | 11/2019 | Hilliard, Jr. | |
| 2020/0000686 A1 | 1/2020 | Swaile | |
| 2020/0000694 A9 | 1/2020 | Sturgis | |
| 2020/0289396 A1 | 9/2020 | Jones et al. | |
| 2020/0289399 A1 | 9/2020 | Jones et al. | |

FOREIGN PATENT DOCUMENTS

| | | | |
|---|---|---|---|
| DE | 102007027781 A1 | 12/2008 | |
| DE | 102018209853 A1 | 12/2019 | |
| EP | 1799189 B1 | 5/2010 | |
| WO | WO0166078 A1 | 9/2001 | |
| WO | WO2016012420 A2 | 1/2016 | |
| WO | WO2017080945 A1 | 5/2017 | |
| WO | WO2018099931 A1 | 6/2018 | |
| WO | WO2018130380 A1 | 7/2018 | |

OTHER PUBLICATIONS

International Search Report and Written Opinion; Application Ser. No. PCT/US2020/020902; dated May 7, 2020, 18 pages.

WS, title: Polyqual or Not? Science-y Hair Blog, posted Nov. 6, 2013 (Year: 2013).

Database WPI; Week 201310; Thomson Scientific, London, GB; AN 2012-Q23352; XP002791192, & CN 102 640 910 A (Zhangjiajie Sisixiang; Food Co Ltd) Aug. 22, 2012 (Aug. 22, 2012)* abstract*.

Database WPI; Week 201779; Thomson Scientific, London, GB; AN 2017-75330D; XP002791191, & CN 107 285 946 A (Chengdu Lucheng Sci & Technology Co Ltd) Oct. 24, 2017 (Oct. 24, 2017)* abstract*.

Extended European Search Report; Application No. 19162396.6-1114; dated Jun. 18, 2019; 8 pages.

Extended European Search Report; Application No. 19162397.4-1114; dated Jul. 2, 2019; 12 pages.

Extended European Search Report; Application No. 19162398.2-1114; dated Jul. 2, 2019; 13 pages.

Gonzalez et al.,"Determining the influence of N-acetylation on water sorption in chitosan films", Carbohydrate Polymers, vol. 133, Year 2015, pp. 110-116.

Moses et al., "Evaluation of functional and pasting properties of different corn starch flours", International Journal of Food Science and Nutrition, vol. 3, No. 6, Nov. 2018, pp. 95-99.

* cited by examiner

ANHYDROUS COSMETIC COMPOSITIONS AND USES

FIELD OF THE INVENTION

The present application generally relates to an anhydrous cosmetic composition and its uses. The anhydrous cosmetic composition includes one or more water-absorbing components; a malodour-controlling component; and a cosmetically acceptable carrier. The anhydrous cosmetic composition is essentially free of aluminum-based antiperspirant actives. The anhydrous cosmetic composition is characterized by a specific combination of a burst resistance pressure greater than about 137.9 mBar (2 psi) according to the Burst Resistance Pressure Test Method as disclosed hereinafter, and a water vapor sorption per 100 g of the composition from about 2.0 g to about 15 g, as measured according to the Water Vapor Sorption Test Method as disclosed hereinafter.

BACKGROUND OF THE INVENTION

Many antiperspirant and deodorants use actives that are astringent metallic salts, or in particular, aluminum-based antiperspirant actives such as aluminum and/or aluminum-zirconium salts. While aluminum and/or aluminum-zirconium salts are highly effective as actives, there is a consumer interest in deodorants that do not contain any aluminum and/or aluminum-zirconium salts.

Superabsorbent polymers are ingredients used in skin care compositions, and other product usages, for instance in US 2016/0374933 A1. Superabsorbent polymers are known to enhance the skin feel during application, and to provide better spreading during application, less stickiness, less shine, and a less oily or greasy look and feel.

Deodorant compositions which are free of aluminum and/or aluminum-zirconium salts have been already commercialized, for example Schmidt's Bergamot+Lime natural deodorant stick. Schmidt's Bergamot+Lime natural deodorant stick is free of aluminum-based antiperspirant actives. The Schmidt's Bergamot+Lime natural deodorant stick is available via the Database GNPD [Online] Mintel; August 2018 (2018-08) "Bergamot+Lime natural deodorant stick", Database accession no. 5918775.

There is a need to provide an anhydrous cosmetic composition for providing consumer malodour protection and dryness control on par or greater than some of the commonly used commercial deodorants and antiperspirants available today.

There is also a need to provide an anhydrous cosmetic composition that can provide a delightful sensory experience at application and through the full day.

There is still a need to provide deodorants that do not contain any aluminum and/or aluminum-zirconium salts with higher malodour protection and dryness control benefits than the corresponding deodorants available today.

SUMMARY OF THE INVENTION

An anhydrous cosmetic composition, or an anhydrous deodorant composition, is provided and comprises:
(a) one or more water-absorbing components;
(b) a malodour-controlling component;
(c) a cosmetically acceptable carrier;
wherein the anhydrous cosmetic composition has a burst resistance pressure greater than about 137.9 mBar (2 psi), or greater than about 206.8 mBar (3 psi), or greater than about 275.8 mBar (4 psi), or from about 275.8 mBar to about 689.5 mBar (4 to 10 psi), as measured according to the Burst Resistance Pressure Test Method as disclosed herein;
wherein the anhydrous cosmetic composition has a water vapor sorption per 100 g of the composition from about 2.0 g to about 15 g, or from about 2.5 g to about 12 g, or from about 3.5 g to about 12 g, or from about 5 g to about 10 g as measured according to the Water Vapor Sorption Test Method as disclosed herein; and
wherein the anhydrous cosmetic composition is essentially free of aluminium-based antiperspirant actives.

The anhydrous cosmetic composition as set out hereinafter may be a deodorant.

The anhydrous cosmetic composition as set out hereinafter may form a film, wherein the film is an adhesive film on the axillary skin surface.

The anhydrous cosmetic composition as set out hereinafter may be an antimicrobial composition.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions of Terms

Figure 1:
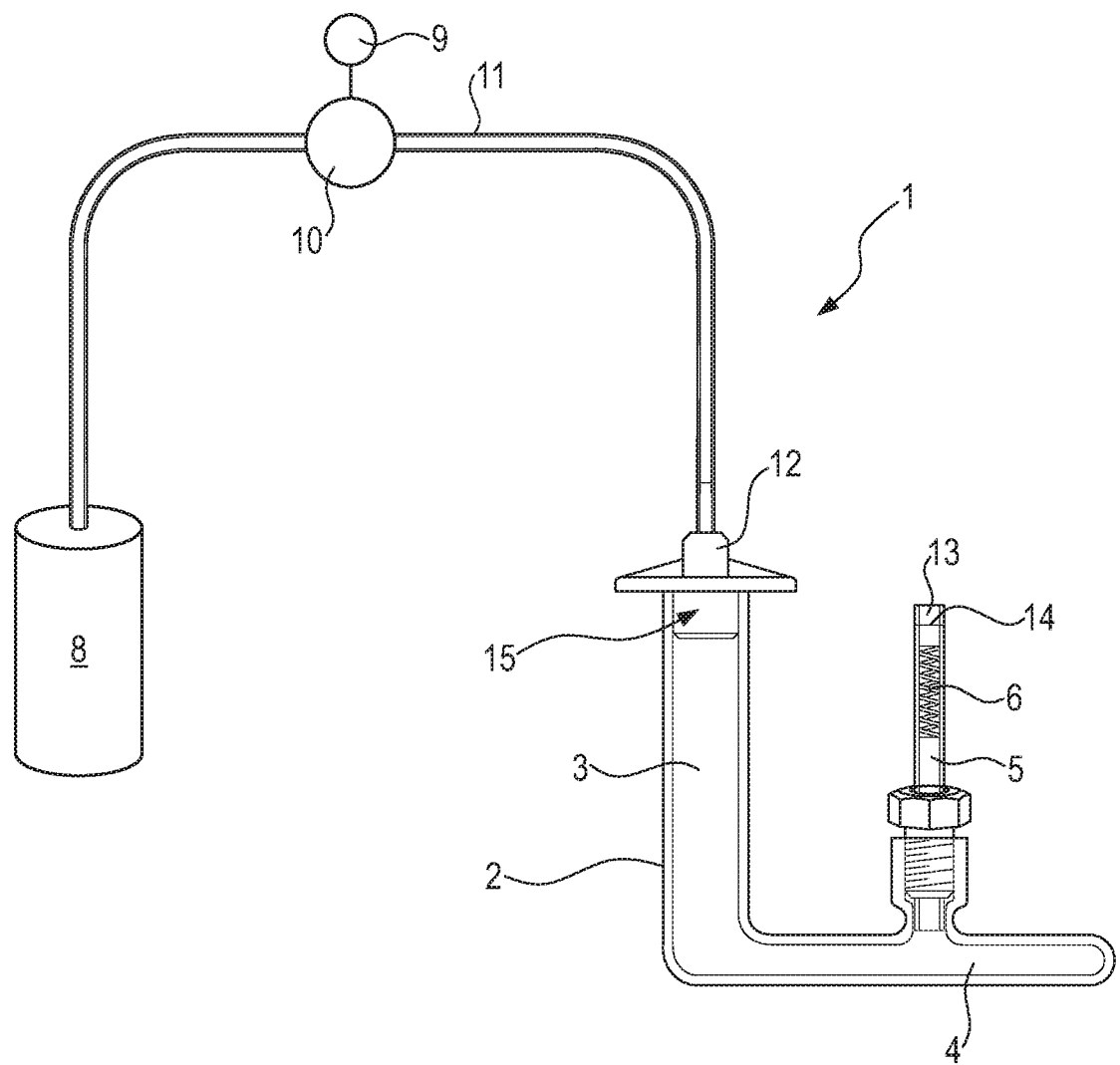
FIG. 1 represents the scheme of an apparatus used to measure the burst resistance pressure.

In this document, including in all embodiments of all aspects of the present invention, the following definitions apply unless specifically stated otherwise.

All percentages are by weight (w/w) of the respective composition, unless otherwise specified. All ratios or percentages are weight ratios or weight percentages unless specifically stated otherwise. "% wt." means percentage by weight. References to "parts" e.g. a mixture of 1 part X and 3 parts Y, is a ratio by weight.

"QSP" or "q.s." means sufficient quantity for 100% or for 100 g. "+/−" indicates the standard deviation. All ranges are inclusive and combinable. The number of significant digits conveys neither a limitation on the indicated amount nor on the accuracy of the measurement.

All measurements are understood to be made under ambient conditions, where "ambient conditions" means at 20° C. at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ("solids") and do not include carriers or by-products that may be included in commercially available materials.

Herein, "comprising" means that other steps and other ingredients can be included in addition. "Comprising" encompasses the terms "consisting of" and "consisting essentially of". The compositions, methods, and uses of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

The terms "include," "includes," and "including," as used herein are meant to be non-limiting.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the composition.

The term "anhydrous" as used herein means that the cosmetic composition is substantially or completely free of separately added water (i.e., anhydrous). Too much added water may result in several deleterious effects such as: 1) increasing the propensity for the water-absorbing components to agglomerate (thereby leading to gritty in-use application feel drawbacks) and 2) potentially driving phase separation issues over time and with increased temperature. It should be appreciated that even an anhydrous cosmetic composition may still contain some water that is bound within an ingredient (e.g., water-absorbing component, superabsorbent polymer, tapioca starch material, etc.) other than intentionally added to the anhydrous cosmetic composition.

The term "substantially free of" as used herein means less than about 1%, less than about 0.8%, less than about 0.5%, less than about 0.3%, or less than about 0.01% of an ingredient by total weight of the composition.

The term "free of" as used herein means that the composition comprises 0% of an ingredient by total weight of the composition.

The term "deodorant" as used herein means a cosmetic composition applied topically at the underarm skin for minimizing malodours or unpleasant odors caused by the interaction of sebum, perspiration and bacteria on the underarm skin.

The term "copolymer" as used herein refers to a polymer derived from two or more polymerizable monomers. When used in generic terms, the term "copolymer" is also inclusive of more than two distinct monomers, for example, terpolymers.

The term "cosmetically acceptable" as used herein means that the compositions, or components described are suitable for use in contact with human skin tissue, especially underarm skin without undue toxicity, incompatibility, instability, allergic response, and the like. All compositions described herein which have the purpose of being directly applied to skin tissue are limited to those being cosmetically acceptable.

The term "mixtures" as used herein is meant to include a simple combination of materials and any compounds that may result from their combination.

The term "molecular weight" or "M.Wt." as used herein refers to the weight average molecular weight unless otherwise stated. The weight average molecular weight of a polymer can be measured by gel permeation chromatography.

The term "superabsorbent polymer" as used herein means a polymer which is capable, in its dry state, of spontaneously absorbing at least about 20 times its own weight of aqueous fluid, in particular of water and especially of distilled water. Such superabsorbent polymers are described in the work "Absorbent Polymer Technology, Studies in Polymer Science 8" by L. Brannon-Pappas and R. Harland, published by Elsevier, 1990.

The term "structurant" as used herein means any material known or otherwise effective in providing suspending, gelling, viscosifying, solidifying, and/or thickening properties to the composition or which otherwise provide structure to the final product form.

Benefits Without being bound by theory, the inventors of the present invention have surprisingly found an improved anhydrous cosmetic composition in terms of improved deodorant performance over e.g. the commercially available Schmidt's Bergamot+Lime natural deodorant stick, when providing a composition having a burst resistance pressure greater than about 137.9 mBar (2 psi) and a water vapor sorption per 100 g of the composition from about 2.0 g to about 15 g. The anhydrous cosmetic composition as set out hereinafter can synergistically help to manage axillary-related dryness and malodour control by forming a relatively strong spreading, wetting and/or adhesive film onto the axillary (underarm) skin surface.

Without being bound by theory, it has been found that the anhydrous cosmetic composition when applied to the axillary skin surface can be resilient to emerging sweat and transepidermal water bond-breaking and solubilizing properties between the axillary skin and the anhydrous cosmetic composition. Any subsequent solubilization of the anhydrous cosmetic composition within the emerging sweat and transepidermal water, and any transfer to undershirt or dress shirt can be thus prevented.

The anhydrous cosmetic composition when forming such an efficient spreading, wetting and adhesive film onto the axillary skin surface, can therefore help prevent or slow down the potential for sweat and transepidermal water to emerge on top of the anhydrous cosmetic composition and axillary skin surface.

In addition, if any sweat and transepidermal water does migrate on top of the anhydrous cosmetic composition and axillary skin surface (e.g. from areas surrounding the axilla and not covered by product), then the surface properties of the anhydrous cosmetic composition as a film can subsequently effectively spread, and adsorb and/or absorb the sweat and transepidermal water onto or into the surface of the film made of the anhydrous cosmetic composition. The sweat and transepidermal water can then be either efficiently bound by the anhydrous cosmetic composition (i.e. it is neither free nor active sweat or transepidermal water which can subsequently start to dissolve the anhydrous cosmetic composition) and/or can be allowed to molecularly evaporate into the axillary cavity but importantly it is not allowed to cohesively ball and coalesce on the product surface into liquid droplets.

Improved deodorant performance have been assessed in-vitro in terms of increased burst resistance pressure. The burst resistance pressure indicates the pressure required to dislodge a fixed amount of the anhydrous cosmetic composition from a glass capillary, by artificial Eccrine sweat under pressure that is channeled to the base of the anhydrous cosmetic composition held within the glass capillary. A specimen plug of composition is loaded into a glass capillary, and the lower surface is exposed to artificial eccrine sweat. The glass capillary system has surface energy properties very close to axillary skin surface energies and seen as a good model for axillary skin.

|  | Nonpolar | Polar |
| --- | --- | --- |
| Average Human Axilla Skin Surface Energy | 29.59 | 3.02 |
| Cyclo-capillary | 29.1 | 4.8 |

After a fixed interaction time, the fluid hydrostatic pressure of the eccrine sweat is increased in a controlled way until the plug of composition is visibly dislodged. The pressure at which the composition is observed to have become dislodged is reported as the burst resistance pressure. In other words, the burst resistance pressure characterizes the resistance property of the anhydrous cosmetic composition to artificial eccrine sweat flow under pressure. The resistance property is measured and quantified as a pressure, i.e. the burst resistance pressure.

The burst resistance pressure characterizes the initial spread and interaction of the anhydrous cosmetic composition onto and with the axillary (underarm) skin surface. Also, the burst resistance pressure characterizes the ability of the established adhesive and cohesive properties of the anhydrous cosmetic composition to resist the solubilization and hydrostatic pressure created by the Eccrine sweat beneath the anhydrous cosmetic composition, to subsequently control dryness perception at the underarm skin area, preferably throughout the full day. The burst resistance pressure characterizes the ability of the film made of the anhydrous cosmetic composition to be resilient to the emerging sweat and transepidermal water that can potentially break the bonding interaction between the anhydrous cosmetic composition and the axillary skin surface; and solubilize the anhydrous cosmetic composition.

Improved deodorant performance of the anhydrous cosmetic composition has been assessed in-vitro in terms of Water Vapor Sorption analysis for assessing the potential for the anhydrous cosmetic composition to uptake and adsorb and/or absorb atmospheric moisture (relative humidity, water vapor). The potential for the anhydrous cosmetic composition to effectively cover the axillary skin surface, spread and adsorb and/or absorb the emerging sweat and transepidermal water generated from the axillary (underarm) skin is in-vitro assessed in terms of the maximum amount of water vapor sorption per 100 g of the composition, when product is exposed to the conditions as outlined by the Water Vapor Sorption Test Method.

Improved deodorant performance of the anhydrous cosmetic composition may be assessed in-vitro in terms of dryness control with the potential of the anhydrous cosmetic composition to effectively provide a barrier, namely absorb and/or adsorb the emerging sweat and transepidermal water generated from the axillary (underarm) skin in terms of par or increased percent water vapor transmission rate reduction (% $WVTR_{red}$), versus commonly used commercial deodorants and antiperspirants free of aluminum and/or aluminum zirconium salts.

The anhydrous cosmetic composition as set out hereinafter can provide an efficient axillary skin film that can facilitate the effective spread and subsequent adsorption and/or absorption and binding of the emerging sweat and transepidermal water.

As a result, the anhydrous cosmetic composition can help for preventing the coalescence of emerging sweat and transepidermal water droplets that can readily be mass transferred as liquid onto consumer textiles, e.g. onto undershirt or dress shirt and forming a visible wet patch. Over time, this then allows for molecular evaporation of spread and/or bound sweat and transepidermal water, with subsequent vaporization and gaseous release into the axillary cavity and out through the porous consumer textile (e.g. undershirt, dress shirt) to prevent the formation of any visible wet patch or any sensory wetness feeling. Overall, the anhydrous cosmetic composition can help significantly improve the overall consumer dryness perception and malodour control at the axillary skin area, across the full day.

The inventors have also found that the anhydrous cosmetic composition when applied topically at the underarm skin, can help minimize the axillary malodours caused by bacteria, sebum and sweat interactions at the underarm skin surface, by adsorbing and/or absorbing and binding any free and unbound water, thus restricting the ability for the bacteria to use any free unbound water to solubilize, digest and metabolize their food (e.g. sweat ingredients and follicular sebum) into small, volatile and very noticeable malodour molecules.

Also, the inventors have found that the anhydrous cosmetic composition can provide a delightful sensory experience at application and preferably through the full day, in terms of improved overall product feel, improved overall application experience, reduced sticky and/or greasy feel while applying the composition and/or while wearing the composition.

The anhydrous cosmetic composition when forming a spreading, wetting and adhesive film onto the axillary skin surface results in consumer malodour protection and dryness control on par or greater than some of the commonly used commercial deodorants and antiperspirants available today that may or may not comprise aluminum and/or aluminum-zirconium salts.

Disclaimer

The anhydrous cosmetic composition is essentially free of aluminum-based antiperspirant actives, or free of aluminum-based antiperspirant actives.

The term "essentially free of aluminum-based antiperspirant actives" means herein that aluminum-based antiperspirant actives are not added to the anhydrous cosmetic composition in any amount that could display some antiperspirant/deodorant effect.

The term "essentially free of aluminum-based antiperspirant actives" as used herein means that the anhydrous cosmetic composition contains less than about 0.05% wt., or less than about 0.01% wt. of one or more of aluminum-based antiperspirant actives by total weight of the anhydrous cosmetic composition.

The term "free of aluminum-based antiperspirant actives" as used herein means that the anhydrous cosmetic composition contains no aluminum-based antiperspirant actives.

Non-limiting examples of aluminum-based antiperspirant actives, include those listed in US antiperspirant monograph, such as, for example, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, aluminum zirconium trichlorohydrex gly, aluminum hydrochloride, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol.

The anhydrous cosmetic composition may not comprise any aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, aluminum zirconium trichlorohydrex gly, aluminum hydrochloride, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol as antiperspirant active component.

Anhydrous Cosmetic Composition

An anhydrous cosmetic composition, or an anhydrous deodorant composition, is provided and comprises:
(a) one or more water-absorbing components;
(b) a malodour-controlling component;
(c) a cosmetically acceptable carrier;
wherein the anhydrous cosmetic composition is essentially free of aluminium-based antiperspirant actives.

The anhydrous cosmetic composition as described hereinbefore has a burst resistance pressure greater than about 137.9 mBar (2 psi), or greater than about 206.8 mBar (3 psi), or greater than about 275.8 mBar (4 psi), or from about 275.8 mBar to about 689.5 mbar (from 4 psi to 10 psi) as measured according to the Burst Resistance Pressure Test Method.

Also, the anhydrous cosmetic composition as described hereinbefore has a water vapor sorption per 100 g from about 2.0 g to about 15 g, or from about 2.5 g to about 12 g, or from about 3.5 g to about 12 g, or from about 5 g to about 10 g as measured according to the Water Vapor Sorption Test Method.

Also, or alternatively, the anhydrous cosmetic composition as described hereinbefore may have a percent water vapor transmission rate reduction (% $WVTR_{red}$) from about 20% to about 50%, or from about 25% to about 45%, or from about 30% to about 40% as measured according to the Water Vapor Transmission Rate Test Method.

The one or more water-absorbing components of the anhydrous cosmetic composition may comprise:
(a1) a first water-absorbing component having a water vapor sorption greater than about 20 g per 100 g of the first water-absorbing component according to the Water Vapor Sorption Test Method as disclosed herein; and
(a2) a second water-absorbing component having a water vapor sorption from about 8.5 g to about 19.9 g per 100 g of the second water-absorbing component according to the Water Vapor Sorption Test Method as disclosed herein.

Also, the one or more water-absorbing components of the anhydrous cosmetic composition may further comprise (a3) a third water-absorbing component having a water vapor sorption from about 2.0 g to about 8.4 g per 100 g of the third water-absorbing component according to the Water Vapor Sorption Test Method as disclosed herein.

Each of the first, second and third water-absorbing components will be described more into details below.

First Water-Absorbing Component

The first water-absorbing component may have a water vapor sorption greater than about 20 g per 100 g of the first water-absorbing component, or from about 20 g to about 80 g per 100 g of the first water-absorbing component, or from about 30 g to about 50 g per 100 g of the first water-absorbing component according to the Water Vapor Sorption Test Method as disclosed herein.

The first water-absorbing component may be selected from the group consisting of a superabsorbent polymer, a polyquaternium, and combination thereof.

The anhydrous cosmetic composition may comprise from about 0.1% to about 20% of the first water-absorbing component, by total weight of the composition, or from about 0.5% to about 15% of the first water-absorbing component, by total weight of the composition, or from about 1.0% to about 10% of the first water-absorbing component, by total weight of the composition.

Superabsorbent Polymer

The first water-absorbing component of the anhydrous cosmetic composition may comprise, or may consist of, a superabsorbent polymer.

The superabsorbent polymer may be present in the anhydrous cosmetic composition ranging from about 0.1% to about 10% by weight, or from about 0.2% to about 8% by weight, or from about 0.4% to about 5% by weight with respect to the total weight of the composition.

The superabsorbent polymers have a high capacity for adsorbing and/or absorbing and retaining water vapor and aqueous fluids, such as eccrine sweat, apocrine sweat and transepidermal water. After adsorbing and/or absorption of the aqueous liquid, the superabsorbent polymers if in a particle form, thus impregnated with aqueous fluid remain insoluble in the aqueous fluid and thus retain their separated particulate state.

The superabsorbent polymers may be linear or cross-linked acrylic homo- or copolymers and derivatives which are neutralized and which are provided in the particulate form.

The superabsorbent polymer may be selected from the group consisting of sodium polyacrylate, sodium polyacrylate starch, sodium acrylates crosspolymer-2, sodium carboxymethyl starch, sodium carbomer, and mixtures thereof. As preferred, the superabsorbent polymer may comprise sodium polyacrylate starch.

Suitable sodium polyacrylates, may be, for example, those sold under the names Octacare X100, X110 and RM100 by Avecia, those sold under the names Flocare GB300 and Flosorb 500 by SNF, those sold under the names Luquasorb 1003, Luquasorb 1010, Luquasorb 1280 and Luquasorb 1100 by BASF, those sold under the names Water Lock G400 and G430 (INCI name: Acrylamide/Sodium Acrylate Copolymer) by Grain Processing, or Aqua Keep 10 SH NF, Aqua Keep 10 SH NFC, sodium acrylate crosspolymer-2, provided by Sumitomo Seika, starches grafted by an acrylic polymer (homopolymer or copolymer) and in particular by sodium polyacrylate, such as those sold under the names Sanfresh ST-100C, ST100MC and IM-300MC by Sanyo Chemical Industries (INCI name: Sodium Polyacrylate Starch), hydrolysed starches grafted by an acrylic polymer (homopolymer or copolymer), in particular the acrylo-acrylamide/sodium acrylate copolymer, such as those sold under the names Water Lock A-240, A-180, B-204, D-223, A-100, C-200 and D-223 by Grain Processing (INCI name: Starch/Acrylamide/Sodium Acrylate Copolymer).

Superabsorbent polymers may include starch grafted polymer or copolymers such as sodium polyacrylate starch; sodium carboxymethyl starch; hydrolysed starches grafted by an acrylic polymer or copolymer such as acryloacrylamide/sodium acrylate copolymer; starch/acrylates/acrylamide copolymer; and combinations thereof.

The superabsorbent polymer may comprise sodium polyacrylate starch. Preferred superabsorbent polymers include Makimousse-7, Makimousse-12, Makimousse-25 and Makimousse-400 supplied by Kobo Products Inc.

The superabsorbent polymers as listed above have a water vapor sorption greater than about 20 g per 100 g of the first water-absorbing component according to the Water Vapor Sorption Test Method as disclosed herein. For instance, sodium polyacrylate starch such as Makimousse-12 has a water vapor sorption per 100 g of 45.05 g. Sodium polyacrylate starch such as Makimousse-7 has a water vapor sorption per 100 g of 41.14 g.

The superabsorbent polymer can help increase the burst resistance pressure of the anhydrous cosmetic composition. The superabsorbent polymer together with a second water-absorbing component as defined hereinafter can help for providing improved adhesive and cohesive properties of the anhydrous cosmetic composition with the axillary skin to control dryness and malodour at the axillary skin.

Preferred, the one or more water-absorbing components may comprise a first water-absorbing component comprising, or consisting of, a superabsorbent polymer, and a second water-absorbing component comprising chitosan as defined hereinafter.

When combined with a superabsorbent polymer, chitosan may have a degree of deacetylation from about 50% to about 99%, or from about 60% to about 95%, or from about 70% to about 90%, or from about 75% to about 85% according to the Degree of Deacetylation Test Method as disclosed herein.

In addition, chitosan may have a viscosity below about 20 mPa·s$^{-1}$ (20 cPs), or from about 2 mPa·s$^{-1}$ (2 cPs) to about 18 mPa·s$^{-1}$ (18 cPs), or from about 5 mPa·s$^{-1}$ (5 cPs) to about 15 mPa·s$^{-1}$ (15 cPs), or from about 5 mPa·s$^{-1}$ (5 cPs) to about 10 mPa·s$^{-1}$ (10 cPs) according to the viscosity Test Method as disclosed herein.

Also, or alternatively, chitosan may have a weight average molecular weight from about 30 kDa to about 150 kDa, or from about 35 kDa to about 100 kDa, or from about 40 kDa to about 80 kDa, according to the Molecular Weight Test Method Chitosan may be available as e.g. ChitoClear® from Primex ehf, Iceland. In the case of chitosan, it has been surprisingly found that the combination of chitosan as defined above and a superabsorbent polymer can help to increase the burst resistance pressure to form a relatively strong spreading, wetting and/or adhesive film onto the surface of the axillary (underarm) skin surface.

Also, the combination of chitosan as defined above and a superabsorbent polymer can help to even more increase the amount of water vapor sorption by the anhydrous cosmetic composition, which can lead to an increased dryness at the axillary (underarm) skin surface.

Furthermore, the combination of chitosan as defined above and a superabsorbent polymer can help to increase the percent WVTR reduction (% $WVTR_{red}$), which is also a characterization of increased dryness.

Polyquaternium

Alternatively, the first water-absorbing component of the anhydrous cosmetic composition may comprise, or may consist of, a polyquaternium.

Polyquaternium may be present in the anhydrous cosmetic composition ranging from about 0.5% to about 20% by weight, or from about 1.0% to about 10% by weight, or from about 2% to about 8% by weight with respect to the total weight of the composition.

Polyquaternium may be selected from the group consisting of polyquaternium-7, polyquaternium-6, polyquaternium-5, polyquaternium-4, polyquaternium-10, polyquaternium-11, polyquaternium-16, polyquaternium-22, polyquaternium-29, polyquaternium-39, polyquaternium-44, polyquaternium-46, and combinations thereof. Preferred, polyquaternium may be selected from the group consisting of polyquaternium-6, polyquaternium-5, polyquaternium-10, and combinations thereof. Preferred, polyquaternium may comprise polyquaternium-6.

Polyquaternium-7 is the polymeric quaternary ammonium salt of acrylamide and diallyldimethyl ammonium chloride.

Polyquaternium-6 is a polymeric quaternary ammonium salt of diallyldimethyl ammonium chloride (q.v.), or Poly(Dimethyl Diallyl Ammonium Chloride) (PolyDADMAC).

Polyquaternium-5 is the polymeric quaternary ammonium salt of acrylamide and beta-methacrylyloxyethyl trimethyl ammonium methosulfate.

Polyquaternium-4 is a the polymeric quaternary ammonium salt of hydroxyethylcellulose quaternized with diallyldimethyl ammonium chloride (q.v.).

Polyquaternium-10 is a polymeric quaternary ammonium salt of hydroxyethyl cellulose reacted with 2,3-epoxypropyltrimonium Chloride (q.v.).

Polyquaternium-11 is the polymeric quaternary ammonium salt formed by the reaction of diethyl sulfate and a copolymer of vinyl pyrrolidone and dimethyl aminoethylmethacrylate.

Polyquaternium-16 is a polymeric quaternary ammonium salt formed from methylvinylimidazolium chloride and vinylpyrrolidone.

Polyquaternium-22 is a copolymer of diallyldimethyl ammonium chloride (q.v.) and acrylic acid in which some of the acrylic acid units may exist in the salt form.

Polyquaternium-29 is the polymeric quaternary ammonium salt of chitosan (q.v.) reacted with propylene oxide and quaternized with epichlorohydrin.

Polyquaternium-39 is a polymeric quaternary ammonium salt of diallyldimethyl ammonium chloride (q.v.), acrylamide and acrylic acid in which some of the acrylic acid units may exist in the salt form.

Polyquaternium-44 is the polymeric quaternary ammonium salt consisting of vinylpyrrolidone and quaternized imidazoline monomers.

Polyquaternium-46 is a polymeric quaternary ammonium salt prepared by the reaction of N-Vinyl Caprolactam (q.v.) and vinylpyrrolidone with methylvinylimidazolium methosulfate.

When used, polyquaternium, or polyquaternium-6 may be in a particulate form, or polyquaternium-6 may be in an anhydrous particulate form and with a weight-average particle size of from about 20 µm to about 120 µm, or from about 35 µm to about 100 µm, or from about 50 µm to about 70 µm according to the Weight Average Particle Size Test Method as disclosed herein.

The polyquaternium as listed above may have a water vapor sorption greater than about 20 g per 100 g of the first water-absorbing component according to the Water Vapor Sorption Test Method as disclosed herein. For instance, polyquaternium such as Polyquaternium-6 has a water vapor sorption per 100 g of 33.67 g.

The addition of polyquaternium can help for improving the spreading, wetting and adhesive film properties of the composition onto the axillary (underarm) skin surface. The efficient spreading, wetting and adhesive film onto the axillary skin surface can help prevent or slow down the emergence of sweat and transepidermal water, and slow down the potential for sweat and transepidermal water to emerge on top of the product and axillary skin surface.

Also, polyquaternium can help for increasing the amount of water vapor sorption per 100 g of the anhydrous cosmetic composition, i.e. increasing the amount of water vapor that is adsorbed or absorbed onto and into the anhydrous cosmetic composition when between being conditioned with a first environmental state and a second environmental state at elevated temperature and humidity.

Combination of a Superabsorbent Polymer and a Polyquaernium

Alternatively, the first water-absorbing component of the anhydrous cosmetic composition may comprise a combination of a superabsorbent polymer and a polyquaternium.

The first water-absorbing component may comprise a mixture of a superabsorbent polymer and a polyquaternium; wherein the superabsorbent polymer is selected from the group consisting of sodium polyacrylate, sodium polyacrylate starch, sodium acrylates crosspolymer-2, sodium carboxymethyl starch, sodium carbomer, and mixtures thereof, or wherein the superabsorbent polymer comprises sodium polyacrylate starch; and wherein polyquaternium is selected from the group consisting of polyquaternium-7, polyquaternium-6, polyquaternium-5, polyquaternium-4, polyquaternium-10, polyquaternium-11, polyquaternium-16, polyquaternium-22, polyquaternium-29, polyquaternium-39, polyquaternium-44, polyquaternium-46, and combinations thereof, or wherein polyquaternium is selected from the group consisting of polyquaternium-6, polyquaternium-5, polyquaternium-10, and combinations thereof, or wherein polyquaternium comprises polyquaternium-6.

The first water-absorbing component may comprise a mixture of sodium polyacrylate starch (e.g. Makimousse-7, Makimousse-12, Makimousse-20, Makimousse-25 or Makimousse-400) and a polyquaternium selected from the group consisting of polyquaternium-5, polyquaternium-6 and polyquaternium-10, or a mixture of sodium polyacrylate starch and polyquaternium-6.

In addition, any polyquaternium as defined above, or polyquaternium-5, polyquaternium-6 or polyquaternium-10, or polyquaternium-6 may be in a particulate form, or polyquaternium-6 may be in an anhydrous particulate form and with a weight-average particle size of from about 20 m to about 120 μm, or from about 35 μm to about 100 μm, or from about 50 μm to about 70 μm according to the Weight Average Particle Size Test Method as disclosed herein.

The superabsorbent polymer can help for increasing the burst resistance pressure of the anhydrous cosmetic composition. The superabsorbent polymer together with the polyquaternium can help for providing the spreading, wetting and adhesive film properties of the anhydrous cosmetic composition to control dryness at the axillary skin.

Second Water-Absorbing Component

The anhydrous cosmetic composition, or an anhydrous deodorant composition, comprises a second water-absorbing component having a water vapor sorption from than about 8.5 g to about 19.9 g per 100 of the second water-absorbing component, or from than about 8.7 g to about 19.0 g per 100 of the second water-absorbing component, or from than about 8.9 g to about 18.0 g per 100 of the second water-absorbing component according to the Water Vapor Sorption Test Method as disclosed herein.

The second water-absorbing component may be selected from the group consisting of gum Arabic, tragacanth gum, galactan, guar gum, carob gum, karaya gum, carrageenan, pectin, agar, agarose, quince seed, algal colloid, glycyrrhizinic acid, xanthan gum, dextran, succinoglucan, pullulan, collagen, casein, albumin, gelatin, chitin, chitosan, hyaluronic acid, and combinations thereof.

Also or alternatively, the second water-absorbing component may be selected from the group consisting of sodium alginate, propylene glycol alginate, polyvinyl alcohol, polyvinyl methyl ether-based polymer, polyvinylpyrrolidone, polyvinylpyrrolidone/vinyl acetate, carboxyvinyl polymer, poly(ethyl acrylate), poly(2-hydroxyethyl methacrylate), polyitaconic acid, polyacrylamide, polyisopropylacrylamide, polyethylene imines, and combinations thereof.

Alternatively, the second water-absorbing component may be selected from the group consisting of agar, agarose, xanthan gum, chitin, chitosan, sodium hyaluronate, sodium alginate, polyvinyl alcohol, polyvinylpyrrolidone, polyvinylpyrrolidone/vinyl acetate, carboxyvinyl polymer, carboxymethyl cellulose, methyl cellulose, hydroxypropylmethylcellulose, hydroxyethylcellulose, hydroxypropylcellulose and combinations thereof.

The anhydrous cosmetic composition may comprise from about 0.1% to about 10% by weight of the second water-absorbing component, by total weight of the composition, or from about 0.2% to about 8% by weight of the second water-absorbing component, by total weight of the composition, or from about 0.5% to about 5% by weight of the second water-absorbing component, by total weight of the composition.

Alginates are unbranched copolymers of (1→4)-linked β-D-mannuronic acid and α-L-guluronic acid residues.

Agarose is a linear polysaccharide built up of the repeating disaccharide unit of (1-*3)-linked β-D-galactose and (1→4)-linked 3,6-anhydro-α-L-galactose residues. Agar is a mixture of agarose, and a heterogeneous mixture of smaller molecules called agaropectin.

Xanthan gum is an extracellular polysaccharide produced by the bacterium *Xanthomonas campestris*. The primary structure of xanthan gum consists of the cellulose-like backbone of (1→4)-linked β-DGlcp residues substituted, at O-3 of alternate glucose residues, with a trisaccharide. The trisaccharide consists of the β-D-Manp-(1→4)-β-D-GlcpA-(1→2)-α-D-Manp-(1→unit.

The molecular structure of chitin is similar to that of cellulose, except that the hydroxyl groups at O-2 of the β-D-Glcp residues are substituted with N-acetylamino groups.

Hyaluronic acid and its salts derive from the natural mucopolysaccharide formed by bonding N-acetyl-D-glucosamine with glucuronic acid.

The second water-absorbing component may be selected from the group consisting of chitin, chitosan, sodium hyaluronate, sodium alginate, polyvinyl alcohol, polyvinylpyrrolidone, polyvinylpyrrolidone/vinyl acetate, carboxyvinyl polymer, carboxymethyl cellulose, hydroxypropylmethylcellulose and combinations thereof.

The second water-absorbing component may be selected from the group consisting of chitin, chitosan, sodium hyaluronate, sodium alginate, polyvinylpyrrolidone, polyvinylpyrrolidone/vinyl acetate, carboxyvinyl polymer, hydroxypropylmethylcellulose and combinations thereof.

The second water-absorbing component may be selected from the group consisting of chitin, chitosan, sodium hyaluronate, sodium alginate, polyvinylpyrrolidone, polyvinylpyrrolidone/vinyl acetate, and combinations thereof.

When a second water-absorbing component is combined with a first water-absorbing component, the burst resistance pressure of the anhydrous cosmetic composition is even more increased. The formation of a spreading, wetting and adhesive film onto the axillary skin surface with all the benefits as described hereinbefore is even more promoted.

Also, the amount of water vapor sorption per 100 g of the composition is also even more increased showing the increased potency of the anhydrous cosmetic composition to absorb or adsorb water vapor and thus to control dryness at the axillary (underarm) skin surface.

The second water-absorbing component may comprise chitosan. Chitosan can be defined as a linear polysaccharide comprising randomly distributed β-(1,4)-linked D-glucosamine (deacetylated unit) and N-acetyl D-glucosamine (acetylated unit) and generally has the following structure:

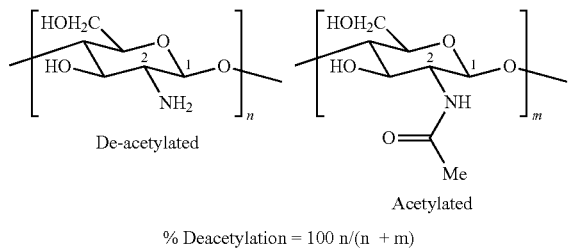

% Deacetylation = 100 n/(n + m)

wherein n and m vary depending on the average molecular weight of the chitosan and the degree of deacetylation of the chitosan. The degree of deacetylation (% deacetylation) of the chitosan is equal to 100n/(n+m).

Chitosan may have a degree of deacetylation from about 50% to about 99%, or from about 60% to about 95%, or from about 70% to about 90%, or from about 75% to about 85% according to the Degree of Deacetylation Test Method as disclosed herein.

In addition, chitosan may have a viscosity below about 20 mPa·s$^{-1}$ (20 cPs), or from about 2 mPa·s$^{-1}$ (2 cPs) to about 18 mPa·s$^{-1}$ (18 cPs), or from about 5 mPa·s$^{-1}$ (5 cPs) to about 15 mPa·s$^{-1}$ (15 cPs), or from about 5 mPa·s$^{-1}$ (5 cPs) to about 10 mPa·s$^{-1}$ (10 cPs) according to the viscosity Test Method as disclosed herein.

Also, or alternatively, chitosan may have a weight average molecular weight from about 30 kDa to about 150 kDa, or from about 35 kDa to about 100 kDa, or from about 40 kDa to about 80 kDa, according to the Molecular Weight Test Method Chitosan may be available as e.g. ChitoClear® from Primex ehf, Iceland. In the case of chitosan, it has been surprisingly found that the addition of chitosan as defined above to a first water-absorbing component being either a superabsorbent polymer or a polyquaternium or a combination of superabsorbent polymer and a polyquaternium can help to increase the burst resistance pressure to form an improved spreading, wetting and adhesive film onto the surface of the axillary (underarm) skin surface.

Also, the addition of chitosan as defined above to a combination of superabsorbent polymer and a polyquaternium can help to even more increase the amount of water vapor sorption by the anhydrous cosmetic composition, which can lead to an increased dryness at the axillary (underarm) skin surface.

Furthermore, the addition of chitosan as defined above to a first water-absorbing component as recited hereinbefore can help to increase the percent WVTR reduction (% $WVTR_{red}$), which is also a characterization of increased dryness.

The second water-absorbing component as listed above have a water vapor sorption from about 8.5 g to about 19.9 g per 100 g of the second water-absorbing component according to the Water Vapor Sorption Test Method as disclosed herein. For instance, polyvinylpyrrolidone has a water vapor sorption per 100 g of 17.18 g. For instance, sodium hyaluronate has a water vapor sorption per 100 g of 15.78 g; sodium alginate has a water vapor sorption per 100 g of 13.75 g, xanthan gum has a water vapor sorption per 100 g of 10.13 g or chitosan has a water vapor sorption per 100 g of 9.44 g.

Optional Third Water-Absorbing Component

The anhydrous cosmetic composition, or an anhydrous r deodorant composition, may comprise a third water-absorbing component having a water vapor sorption from about 2.0 g to about 8.4 g per 100 of the third water-absorbing component, or from about 2.5 g to about 8.3 g per 100 of the third water-absorbing component, or from about 3.0 g to about 8.0 g per 100 of the third water-absorbing component according to the Water Vapor Sorption Test Method as disclosed herein.

The third water-absorbing component may be selected from the group consisting of starch particles, a stearate component, and mixtures thereof.

The anhydrous cosmetic composition may comprise from about 2% to about 25% by weight of the third water-absorbing component, by total weight of the composition, or from about 3% to about 20% by weight of the third water-absorbing component, by total weight of the composition, or from about 3% to about 18% by weight of the third water-absorbing component, by total weight of the composition.

Starch particles may be selected from the group consisting of tapioca starch, corn starch, potato starch, glyceryl starch, calcium starch octenyl succinate, polymethylsilsesquioxane coated tapioca starch, arrowroot starch and combinations thereof. Starch particles may be selected from the group consisting of tapioca starch, corn starch, potato starch, glyceryl starch, arrowroot starch and combinations thereof. Preferred starch particles may comprise tapioca starch.

The starch particles suitable for use herein may be coated or uncoated (e.g., coated with a suitable silicone material). In some instances, the starch particles may be a coated or uncoated starch derivative. Alternatively, the starch particles are hydrophobically coated.

The starch particles herein may have a weight average particle size of from about 1 μm to about 40 μm, or from about 2 μm to about 30 μm, or from about 5 μm to about 30 μm, or from about 5 μm to about 25 μm. The particle size of the starch particles can be determined by any suitable method known in the art, such as by using coulter-counter equipment or the ASTM Designation E20-85, titled "Standard Practice for Particle Size Analysis of Particulate Substances in the Range of 0.2 to 75 Micrometers by Optical Microscopy," ASTM Volume 14.02, 1993.

Some non-limiting examples of commercially available starch particles suitable for use herein are tapioca starch (available as Tapioca Pure from AkzoNobel), corn starch (available as Purity 21C from AkzoNobel), potato starch (available as XyPure PT from Xytrus), glyceryl starch (available as Dry-Flo GS from AkzoNobel), calcium starch octenylsuccinate (available as Skin Flow C from MGP Ingredients, Inc., and Mackaderm CSTO-Dry from Rhodia, Inc.), and polymethylsilsesquioxane coated tapioca starch (available as Dry-Flo TS from AkzoNobel).

Preferred, the starch particles suitable for use herein may be selected from the group consisting of coated starch, uncoated starch, non-crosslinked starch such as tapioca starch (available as Tapioca Pure from AkzoNobel) and polymethylsilsesquioxane coated tapioca starch (available as Dry-Flo TS from AkzoNobel).

Preferred, the starch particles may be non-crosslinked starch particles. Preferred, the starch particles may comprise tapioca starch.

The starch particles can help for modifying the rheologic properties of the composition, and for improving the water vapor sorption properties of the composition and for helping to form a spreading, wetting and adhesive film onto the axillary skin surface in terms of increased burst resistance pressure.

The stearate component may be selected from the group consisting of sucrose monostearate, sucrose distearate, acetylated sucrose distearate, glycol distearate, glycol monostearate, glycerol distearate, glycerol monostearate, glycerol isostearate, sorbitan monostearate, sorbitan distearate, sorbitan tristearate, polyglyceryl-6 distearate, PEG-150 distearate, PEG-8 distearate, propylene glycol isostearate, pentaerythritol tetrastearate and combinations thereof.

The stearate component may be selected from the group consisting of sucrose monostearate, sucrose distearate, acetylated sucrose distearate, glycol distearate, glycol monostearate, glycerol distearate, glycerol monostearate, glycerol isostearate, sorbitan monostearate, sorbitan distearate, sorbitan tristearate, and combinations thereof.

The stearate component may be selected from the group consisting of sucrose monostearate, sucrose distearate, acetylated sucrose distearate, glycol distearate, glycol monostearate, glycerol distearate, glycerol monostearate, and combinations thereof.

The stearate component can help e.g. for impacting the hardness of the composition or the percent water vapor transmission rate reduction (% $WVTR_{red}$) and the amount of water vapor sorption properties of the composition.

Also or alternatively, the third water-absorbing component may comprise a sucrose component, selected from the group consisting of sucrose dilaurate, sucrose distearate, sucrose cocoate, acetylated sucrose distearate, and combinations thereof.

Sucrose monostearate is a mixture of sucrose esters of stearic acid consisting primarily of the monoester. Sucrose distearate is a mixture of sucrose esters of stearic acid consisting primarily of the diester and can be supplied from Croda Europe as Crodesta F110. Glycol distearate is the diester of ethylene glycol and stearic acid. Glycol monostearate is the monoester of ethylene glycol and stearic acid. Glyceryl distearate or glycerol distearate is a diester of glycerin and stearic acid. Glyceryl or glycerol monostearate is a monoester of glycerin and stearic acid. Sorbitan monostearate is the monoester of stearic acid and the hexitol anhydrides derived from sorbitol. Sorbitan distearate is the diester of stearic acid and the hexitol anhydrides derived from sorbitol. Sorbitan tristearate is the triester of stearic acid and the hexitol anhydrides derived from sorbitol.

Preferred, the third water-absorbing component may comprise a mixture of sucrose distearate and tapioca starch. Such combination appears to optimize, namely increasing the burst resistance pressure, the percent water vapor transmission rate reduction (% $WVTR_{red}$) and the amount of water vapor sorption properties of the composition.

The third water-absorbing component as listed above have a water vapor sorption from about 2.0 g to about 8.4 g per 100 g of the third water-absorbing component according to the Water Vapor Sorption Test Method as disclosed herein. For instance, starch particles such as tapioca starch has a water vapor sorption per 100 g of 5.39 g. For instance, stearate components such as sucrose distearate has a water vapor sorption per 100 g of 3.72 g; or glycerol monostearate has a water vapor sorption per 100 g of 3.68 g.

Malodour-Controlling Component

The anhydrous cosmetic composition comprises a malodour-controlling component. A malodour-controlling component may be defined as any topical material that is known or otherwise effective in preventing or eliminating malodour associated with perspiration or with the inherent components of the anhydrous cosmetic composition. Suitable malodour-controlling components may be selected from the group consisting of antimicrobial ingredients, malodour-absorbing material, sebum rheology modifier, perfume malodour-masking materials, and combinations thereof.

The malodour-controlling component may comprise antimicrobial ingredients. The antimicrobial ingredients may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, citric acid, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate such as zinc citrate dihydrate, salicylate or salicylic acid, and piroctose, especially zinc salts, zinc oxide, zinc citrate, zinc carbonate, zinc hydroxide, zinc lactate, zinc gluconate, zinc ricinoleate and acids thereof, heavy metal salts of pyrithione, especially zinc pyrithione, zinc phenolsulfate, farnesol, and combinations thereof.

The malodour-controlling component may comprise antimicrobial ingredients, wherein the antimicrobial ingredients may be selected from the group consisting of 2-Pyridinol-N-oxide (piroctone olamine), lupamin, beryllium carbonate, magnesium carbonate, calcium carbonate, magnesium hydroxide, magnesium hydroxide and magnesium carbonate hydroxide, partially carbonated magnesium hydroxide, potassium carbonate, potassium bicarbonate, sodium carbonate, sodium sesquicarbonate, baking soda, hexamidine, zinc oxide, zinc citrate, zinc citrate dihydrate, zinc carbonate, zinc hydroxide, zinc lactate, zinc gluconate, zinc ricinoleate, thymol, polyvinyl formate, citric acid, salicylic acid, dehydroacetic acid, niacinamide and combinations thereof.

A suitable example of a sebum rheology modifier may be decylene glycol or salicylic acid.

The malodour-controlling component may be selected from the group consisting of 2-Pyridinol-N-oxide, zinc citrate dihydrate, zinc oxide, zinc citrate, zinc carbonate, zinc hydroxide, zinc lactate, zinc gluconate, zinc ricinoleate, decylene glycol, salicylic acid, citric acid, dehydroacetic acid and combinations thereof.

The anhydrous cosmetic composition may comprise from about 0.001% to about 10% by weight of the malodour-controlling component, by total weight of the composition, or from about 0.1% to about 5% by weight of the malodour-controlling component, by total weight of the composition, or from about 0.2% to about 1% by weight of the malodour-controlling component, by total weight of the composition.

Cosmetically Acceptable Carrier

The anhydrous cosmetic compositions disclosed herein typically comprise a cosmetically acceptable carrier.

The cosmetically acceptable carrier may comprise one or more emollients. Depending on the type of product form desired, the anhydrous cosmetic composition may comprise from about 2% to about 35% by weight, of the one or more emollients by total weight of the composition, or from about 10% to about 30% by weight, of the one or more emollients by total weight of the composition, or from about 15% to about 25% by weight, of the one or more emollients by total weight of the composition.

The one or more emollients may comprise plant oils including olive oil, coconut oil, sunflower seed oil, jojoba seed oil, avocado oil, canola oil, corn oil, and mixtures thereof.

Also, or alternatively, one or more emollients may comprise mineral oil, shea butter, PPG-14 butyl ether, isopropyl isostearate, isopropyl myristate, petrolatum, butyl stearate, cetyl octanoate, butyl myristate, myristyl myristate, $C_{12-15}$ alkylbenzoate (e.g., Finsolv™), octyldodecanol, isostearyl isostearate, octododecyl benzoate, isostearyl lactate, isostearyl palmitate, isobutyl stearate, dimethicone copolyol, PEG-12 dimethicone and mixtures thereof.

Preferred, the one or more emollients may be selected from the group consisting of mineral oil, PPG-14 butyl ether, isopropyl isostearate, isopropyl myristate, petrolatum, isododecane, polydecene, $C_{12-15}$ alkylbenzoate, octyldodecanol, isostearyl isostearate, dimethicone copolyol, PEG-12 dimethicone (Silsoft 870, Momentive), PPG-12 dimethicone (Silsoft 900, Momentive) and mixtures thereof.

The anhydrous cosmetic composition may also comprise additional emollients with molecular weights below 750 Daltons to provide a desired feel, to solubilize deodorant actives or fragrances, and to enable solubilization of the one or more structurants during product making. One particular type of additional emollient may be polyhydric alcohols, which are typically added at a level of at most about 30%, by total weight of the composition. Suitable polyhydric alcohols may include, but are not limited to, propylene glycol, dipropylene glycol, tripropylene glycol, low molecular weight polypropylene glycols, ethylene glycol, diethylene glycol, triethylene glycol, PEG-4, PEG-8, 1,2-pentanediol, 1,2-hexanediol, hexylene glycol, trimethylene glycol, glycerin, diglycerin, xylitol, erythritol, sorbitol, trehalose, and combinations thereof.

The anhydrous cosmetic composition may comprise the additional polyhydric alcohol emollients cumulatively at most about 30% by total weight of the composition. The anhydrous cosmetic composition may comprise the polyhydric alcohol emollients cumulatively from 5 about % to about 30%, or from about 10% to about 27%, or from about 15% to about 25%, by total weight of the composition.

Also, or alternatively, the cosmetically acceptable carrier may comprise one or more structurants. The one or more structurants can help for providing the anhydrous cosmetic compositions with the desired viscosity, rheology, texture and/or product hardness, or to otherwise help suspend any dispersed solids or liquids within the composition.

The cosmetically acceptable carrier may comprise one or more structurants. The anhydrous cosmetic composition may comprise from about 1% to about 95% by weight, of the one or more structurants by total weight of the composition, or from about 20% to about 75% by weight, of the one or more structurants by total weight of the composition, or from about 35% to about 45% by weight, of the one or more structurants by total weight of the composition.

The one or more structurants may comprise waxes with melting points between about 50° C. and about 70° C. including Japan wax, lemon wax, grapefruit wax, beeswax, ceresine, paraffin, hydrogenated jojoba, stearyl stearate, palmityl stearate, stearyl behenate, cetearyl behenate, hydrogenated high erucic acid rapeseed oil, cetyl alcohol and stearyl alcohol.

Also, or alternatively the one or more structurants may comprise waxes with melting points above 70° C. include ozokerite, candelilla, carnauba, espartograss, cork wax, guaruma, rice oil wax, sugar cane wax, ouricury, montan ester wax, sunflower wax, shellac, ozokerite microcrystalline wax, sasol wax, polyethylenes, polymethylenes, ethylene glycol dipalmitate, ethylene glycol di(12-hydroxystearate), behenyl behenate, glyceryl tribehenate, hydrogenated castor oil (castor wax), and behenyl alcohol.

Also, or alternatively the one or more structurants may comprise $C_{18}$-$C_{36}$ triglyceride, Fischer-Tropsch waxes, silicone waxes, $C_{30-50}$ alkyl beeswax, $C_{20-40}$ alkyl erucates, $C_{18-38}$ alkyl hydroxy stearoyl stearates, $C_{20-40}$ dialkyl esters of dimer acids, $C_{16-40}$ alkyl stearates, $C_{20-40}$ alkyl stearates, cetyl ester wax, and spermaceti.

Also, or alternatively the one or more structurants may comprise fatty acid gellants such as fatty acid and hydroxyl or alpha hydroxyl fatty acids, having from 10 to 40 carbon atoms, and ester and amides of such gelling agents. Non-limiting examples of such gelling agents include, but are not limited to, 12-hydroxystearic acid, 12-hydroxylauric acid, 16-hydroxyhexadecanoic acid, behenic acid, erucic acid, stearic acid, caprylic acid, lauric acid, isostearic acid, and combinations thereof. Preferred, gelling agents are 12-hydroxystearic acid, esters of 12-hydroxystearic acid, amides of 12-hydroxystearic acid and combinations thereof.

Also, or alternatively the one or more structurants may comprise stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, bayberry, synthetic waxes such as Fisher-Tropsch waxes, and microcrystalline wax; polyethylenes with molecular weight of about 200 to about 1000 daltons; solid triglycerides, caprylic/capric triglyceride; behenyl alcohol, or combinations thereof.

The anhydrous cosmetic composition may further comprise a non-volatile silicone fluid. The non-volatile silicone fluid may function as the primary or principal liquid carrier for the water-absorbing components. As used herein, the term "non-volatile" refers to a material that has a boiling point above about 250° C. (at atmospheric pressure) and/or a vapor pressure below about 0.1 mm Hg at 25° C. Conversely, the term "volatile" refers to a material that has a boiling point less than about 250° C. (at atmospheric pressure) and/or a vapor pressure about 0.1 mm Hg at 25° C.

The non-volatile silicone fluid may be a liquid at or below human skin temperature, or otherwise in liquid form within the anhydrous cosmetic composition during or shortly after topical application. The concentration of the non-volatile silicone may be from about 15% to about 70%, or from about 25% to about 55%, or from about 30% to about 45%, by weight of the composition.

Non-volatile silicone fluids may include those which conform to the formula:

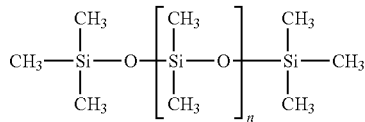

wherein n is greater than or equal to 1, from 6 to 185, from 9 to 125, from 9 to 80, from 9 to 50, from 13 to 50 or from 27 to 50. The non-volatile silicone fluids may generally have viscosity values of from about 3 centistokes to about 350 centistokes, or from about 5 centistokes to about 200 centistokes, or from about 20 centistokes to about 100 centistokes, or from about 50 centistokes to about 80 centistokes, as measured at 25° C. (1 centistoke being equal to $1\times10^{-6}$ $m^2/s$).

Alternatively, the non-volatile silicone fluids may generally have viscosity values of from about 5 centistokes to about 100 centistokes, or from about 5 centistokes to about 50 centistokes, or from about 5 centistokes to about 30 centistokes, as measured at 25° C. (1 centistoke being equal to $1\times10^{-6}$ $m^2/s$).

Some non-volatile, silicone fluids that may be used include, but are not limited to, polyalkyl siloxanes, polyalkylaryl siloxanes, and polyether siloxane copolymers, and mixtures thereof. Some preferred non-volatile silicone fluids may be linear polyalkyl siloxanes, especially polydimethyl siloxanes (e.g., dimethicone).

Specific non-limiting examples of suitable nonvolatile silicone fluids include Dow Corning 200, hexamethyldisiloxane, Dow Corning 225, Dow Corning 1732, Dow Corning 5732, Dow Corning 5750 (available from Dow Corning Corp.); SF-96, SF-1066 and SF18 (350) Silicone Fluids (available from G.E. Silicones); and Xiameter® series like Xiameter® PMX-200 Silicone Fluid 50 cS, or 10 cS, or 5 cS (available from Dow Corning Corp.).

Low surface tension non-volatile solvent may also be used. Such solvents may be selected from the group consisting of dimethicones, dimethicone copolyols, phenyl trimethicones, alkyl dimethicones, alkyl methicones, and mixtures thereof. Low surface tension non-volatile solvents are also described in U.S. Pat. No. 6,835,373 (Kolodzik et al.).

Incorporating a non-volatile silicone fluid in the anhydrous cosmetic composition may provide several benefits. First, the non-volatile silicone fluids can be more effectively deposited on the skin than volatile silicone fluids for forms like aerosol. Deposition of relatively high concentrations of a non-volatile silicone fluid in the anhydrous cosmetic composition can help to reduce visible white residue at application, reduce visible white residue throughout the day and reduce anhydrous cosmetic composition transfer to clothes while dressing.

Optional Components

The anhydrous cosmetic composition may further include any optional component that is known for use in deodorant compositions or other personal care products, or which is otherwise suitable for topical application to human skin, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, or up to about 5% by total weight of the composition.

One example of optional components are perfume and fragrance deliveries. The anhydrous cosmetic compositions herein may include microcapsules. The microcapsules may be any kind of microcapsule disclosed herein or known in the art. The microcapsules may have a shell and a core material encapsulated by the shell. The core material of the microcapsules may include one or more fragrances. The shells of the microcapsules may be made from synthetic polymeric materials or naturally-occurring polymers. The microcapsules may be friable microcapsules. A friable microcapsule is configured to release its core material when its shell is ruptured. The rupture can be caused by forces applied to the shell during mechanical interactions. The microcapsules may have shells made from any material in any size, shape, and configuration known in the art. Some or all of the shells may include a polyacrylate material, such as a polyacrylate random copolymer. The microcapsules may also encapsulate one or more benefit agents. The benefit agent(s) include, but are not limited to, one or more of chromogens, dyes, cooling sensates, warming sensates, fragrances, oils, pigments, in any combination. When the benefit agent includes a fragrance, said fragrance may comprise from about 2% to about 80%, from about 20% to about 70%, from about 30% to about 60% of a perfume raw material with a ClogP greater than about −0.5, or even from about 0.5 to about 4.5. The microcapsules may encapsulate an oil soluble material in addition to the benefit agent. The microcapsule may be spray-dried to form spray-dried microcapsules. The anhydrous cosmetic compositions may also include a parent fragrance and one or more encapsulated fragrances that may or may not differ from the parent fragrance. Some fragrances may be considered to be volatile and other fragrances may be considered to be or non-volatile. Further types and processes regarding microcapsules are disclosed in U.S. Pat. No. 9,687,425.

The anhydrous cosmetic composition may also contain one or more other delivery systems for providing one or more benefit agents, in addition or in place of the microcapsules. The additional delivery system(s) may differ in kind from the microcapsules. For example, wherein the microcapsule are friable and encapsulate a fragrance, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), or combinations thereof. Further details regarding suitable starches and cyclic oligosaccharide are disclosed in U.S. Pat. No. 9,687,425.

The anhydrous cosmetic compositions may include one or more fragrances. As used herein, "fragrance" is used to indicate any odoriferous material. Any fragrance that is cosmetically acceptable may be used in the deodorant compositions. For example, the fragrance may be one that is a liquid at room temperature. Generally, the fragrance(s) may be present at a level from about 0.01% to about 40%, from about 0.1% to about 25%, from about 0.25% to about 20%, or from about 0.5% to about 15%, by total weight of the composition.

A wide variety of chemicals are known as fragrances, including aldehydes, ketones, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolysable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor. Suitable fragrances are also disclosed in U.S. Pat. Nos. 9,687,425, 4,145,184, 4,209,417, 4,515,705, and 4,152,272.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Another example of optional components are clay mineral powders such as talc, mica, laponite, silica, magnesium silicate, silicic acid, silicic anhydride, calcium silicate, zeolite, laponite, and hectorite; pearl pigments such as barium sulfate, calcium secondary phosphate, calcium carbonate, magnesium carbonate, magnesium hydroxide, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, lithium cobalt titanate, titanium oxide coated mica; organic powders such as polyester, polyethylene, polystyrene, methyl methacrylate resin, cellulose, 12-nylon, 6-nylon, styrene-acrylic acid copolymers, polypropylene, vinyl chloride polymer, tetrafluoroethylene polymer, boron nitride, fish scale guanine, laked tar color dyes, laked natural color dyes; and combinations thereof.

Talc, if used at relatively high levels might produce a significant amount of white residue which has been found to be a consumer negative for product acceptance. Therefore, the anhydrous cosmetic composition may comprise from about 0.1% to about 15% by weight of talc by total weight of the composition, or from about 0.1% to about 5% by weight of talc by total weight of the composition, or from about 0.1% to about 3% by weight of talc by total weight of the composition.

Nonlimiting examples of other optional components may include emulsifiers, distributing agents, antimicrobials, pharmaceutical or other topical active, preservatives, surfactants, chelants, astringents, etc. (e.g., clove oil, menthol, camphor, eucalyptus oil, eugenol, menthyl lactate, witch hazel distillate), and so forth. Examples of such optional components are described in U.S. Pat. No. 4,049,792 (Elsnau); U.S. Pat. No. 5,019,375 (Tanner et al.); and U.S. Pat. No. 5,429,816 (Hofrichter et al.).

Method of Manufacture, Product Forms and Uses

The anhydrous cosmetic composition can be made in any suitable manner known in the art, for instance, by following the steps of 1) heating the one or more emollients, the one or more structurants, the optional ingredients when applicable to a temperature between about 60° C. and about 90° C., 2) adding the malodour-controlling component and heating until dissolved, 3) adding between about 70° C. and about 88° C. the third water-absorbent component if applicable, 4) adding the second water-absorbent component, 5) adding the first water-absorbent component, 6) mix until uniform mixture, cool to about 65° C., 7) adding any fragrance or any other labile material, cool to about 60° C., pouring the product into an appropriate container, and 8) allowing the product to cool and solidify.

The anhydrous cosmetic composition can be in the form of a stick product. The stick product may be made by mixing all the components of the products in an open-top or vented tank. Many powders come with bound moisture, especially naturally high moisture powders like starches. In a mostly anhydrous process with waxes, melting the waxes above their melt point can release this bound water as the batch temperature increases. In a closed tank process this water vapor will condense in the tank and drip back into the batch as water. This water can interact with the most water-soluble ingredients in the batch to have negative effects on the product, including releasing the pH of any antimicrobial ingredient, which can then degrade any perfume ingredients in the batch. Additionally, the condensed water can interfere with the wax and produce a stick softer than intended.

To reduce the risk of these negative consequences, the ideal process may be based on the production of the batches in one of four ways:

1. An open tank system where the water vapor can leave the batch tank to reduce or eliminate condensation.
2. A vented closed tank to also remove water vapor during the batch process.
3. A dual phase process where the moisture containing powders can be put into the cold phase separate from the wax phase which is heated. These two phases are then mixed before filling.
4. A low residence time batch process for a closed system, where the product has less than 3 hours residence time above about 50° C. to reduce the rate of reaction from the moisture.

A method of making a deodorant composition or stick may comprise the steps of combining any of the herein described anhydrous cosmetic composition components in an open tank system or a vented closed tank. The components may be mixed, heated, and then cooled into a stick product.

The anhydrous cosmetic composition may be applied to the axillary skin in either a typical contact type product form, e.g., a stick (a solid opaque or translucent or transparent stick) or roll-on, a gel, a cream, a wipe or a typical non-contact type product form, such as an aerosol or a non-aerosol spray.

The anhydrous cosmetic composition may be topically applied to the axilla or other area of the skin in any known or otherwise effective method for controlling malodour associated with perspiration. These methods comprise applying to the axilla or other area of the human skin an effective amount of the anhydrous cosmetic composition, typically about 0.1 gram per axilla to about 2.0 gram per axilla. A method of use could be, for example, applying to a user a leave-on anhydrous cosmetic composition as defined hereinbefore.

The anhydrous cosmetic composition as described hereinbefore can be used for topical application onto the axillary skin surface.

The anhydrous cosmetic composition as described hereinbefore may be a deodorant composition.

The anhydrous cosmetic composition as described hereinbefore may be used as a deodorant composition, wherein the anhydrous cosmetic composition is applied topically at the underarm skin for minimizing malodours or unpleasant odors caused by the interaction of sebum, perspiration and bacteria on or in the underarm skin.

The anhydrous cosmetic composition as described hereinbefore can be used as a deodorant composition for improving a dry axillary skin feel. Indeed, an improved dry axillary skin feel may be characterized by an improvement of softness.

The anhydrous cosmetic composition as described hereinbefore may be used as a deodorant composition, wherein the anhydrous cosmetic composition is applied topically at the underarm skin for providing dryness appearance at the underarm skin.

The anhydrous cosmetic composition as described hereinbefore may be used as a deodorant composition, by forming a film, a spreading, wetting and adhesive film onto the axillary (underarm) skin surface.

The efficient spreading, wetting and adhesive film onto the axillary skin surface can help prevent or slow down the emergence of sweat and transepidermal water. The efficient spreading, wetting and adhesive film onto the axillary skin surface can also help prevent or slow down the potential for sweat and transepidermal water to emerge on top of the product and axillary skin surface.

The anhydrous cosmetic composition as described hereinbefore may be used as a deodorant composition, wherein the anhydrous cosmetic composition is able to control dryness at the axillary skin by spreading, and adsorbing and/or absorbing the released sweat and transepidermal water generated from the axillary skin.

The anhydrous cosmetic composition as described hereinbefore may be an antimicrobial composition.

The anhydrous cosmetic composition may be used as an antimicrobial composition by minimizing the malodours caused by bacteria, by adsorbing and/or absorbing and binding any free and unbound water, thus restricting the ability for the bacteria to use any free unbound water to solubilize, digest and metabolize their food (e.g. sweat ingredients and follicular sebum) into small, volatile malodour molecules.

Test Methods

It is understood that the test methods that are disclosed in the Test Methods Section of the present application should be used to determine the respective values of the parameters of Applicants' invention as such invention is described and claimed herein.

Molecular Weight Test Method

The following test method is used to determine the weight average molecular weight of the chitosan. Size-exclusion liquid chromatography (LC) is used to determine the Weight-Average Molecular Weight of chitosan. Chitosan samples (0.1% wt/vol) are dissolved in AcOH/AcNH$_4$ buffer (pH 4.5) and then filtered through a 0.45 um pore size membrane (Millipore). Size-exclusion liquid chromatography (LC) is performed by means of an LC pump (such as the 1260 Infinity pump, Agilent Technologies, Santa Clara, Calif., USA), with two serially-connected columns specifically a model TSK G2500-PW column and a model TSK G6000-PW column, both available from Tosoh Bioscience LLC (King of Prussia, Pa., USA). The detection is achieved via a differential refractometer (such as the model Wyatt Optilab T-rex) coupled online with a MALLS detector (such as the model Wyatt Dawn Heleos II) both available from Wyatt Technology Corp. (Santa Barbara, Calif., USA.). Degassed AcOH/AcNH$_4$ buffer (pH 4.5) is used as the eluent after two filtrations through 0.22 um pore size membranes (Millipore). The flow rate is maintained at 0.5 mL/min, and the amount of sample injected is 100 µl. Chromatograms are analyzed by the software such as the Wyatt Astra version 6.1.2 (Wyatt Technology Corp., Santa Barbara, Calif., USA) to calculate the Weight Average Molecular Weight of the chitosan sample.

Degree of Deacetylation Test Method

The following test method is used to determine the degree of deacetylation of chitosan. The degree of deacetylation of chitosan test material is determined via Nuclear Magnetic Resonance (NMR) spectroscopy. Chitosan test material (10 mg) is dissolved in 1 mL of dilute acidic D$_2$O (>99.9%, such as available from Aldrich). A Briker NMR instrument model DRX 300 spectrometer (300 MHz) (Bruker Corp., Billerica, Mass., USA) or similar instrument is used to measure the $^1$H NMR at 298 Kelvin. The $^1$H chemical shifts are expressed from the signal of 3-(trimethylsilyl) propionic-2,2,3,3-d$^4$ acid sodium salt (>98%, such as available from Aldrich) which is used as an external reference. The degree of deacetylation is calculated from the measured chemical shifts according to standard and widely used approach described in the publication: Hirai et al., Polymer Bulletin 26 (1991), 87-94.

Viscosity Test Method

The following test method is used to determine the viscosity of the chitosan. The viscosity of chitosan test material is determined by measuring at 25° C. 1% (wt/vol) aqueous solution of the chitosan in deionised (DI) water using a controlled-stress rheometer such as model AR1000 rheometer (TA instruments, New Castle, Del., USA) or equivalent. The instrument is configured using parallel steel plates of 60 mm diameter, and a gap size of 500 am, and a temperature of 25° C. The reported viscosity is the value measured at 1 s$^{-1}$ and at 25° C., during a logarithmic shear rate sweep from 0.06 s$^{-1}$ to 1000 s$^{-1}$ performed during a 1 minute time period.

Burst Resistance Pressure Test Method

The Burst Resistance Pressure Test Method is used to measure the pressure required to dislodge a fixed amount of composition from a glass capillary. A specimen plug of composition is loaded into a glass capillary, and the lower surface is exposed to artificial eccrine sweat. After a fixed interaction time, the fluid pressure of the eccrine sweat is increased in a controlled way until the plug of composition is visibly dislodged. The pressure at which the composition is observed to have become dislodged is reported as the burst resistance pressure. This method is carried out in an environment 23±2° C. and 50±5% relative humidity environment unless otherwise specified, and all materials and apparatus used are allowed to equilibrate to lab conditions for at least two hours prior to use. Formulations that have been fully packed are equilibrated in their unused, unopened state. Experimental formulations that have not been fully packed are equilibrated to the laboratory environment in a sealed glass jar with a headspace volume representing no greater than 25% of the overall jar volume.

Materials and Apparatus

Artificial eccrine sweat mixture solution is prepared by dissolving 0.2 g Bovine Serum Albumin, or BSA, (Biotechnology Grade, Cat. No. 9048-46-8, VWR International, Radnor, Pa., USA, or equivalent) in 100 mL artificial sweat stabilized to pH 4.5±0.5 (Cat. No. 1700-0531, Pickering Laboratories, Inc., Mountain View, Calif., USA, or equivalent) at a level of 0.2 g BSA per 100 mL artificial sweat. This mixture solution can be stored for up to 1 week at 5° C. It is equilibrated to room temperature (ensuring that any solids precipitated in cool storage dissolve) before use.

The apparatus 1 depicted in FIG. 1 is used to perform this method. An L-shaped glass reservoir 2 is positioned such that the main tube 3 is vertically oriented and base 4 extends horizontally. (The diameters and lengths of the main tube 3 and base 4 are not critical, though they must not introduce any consequential pressure drop associated with the small flow of artificial eccrine sweat required to dislodge specimen plugs as described below.) To the horizontally extending base 4 is attached one or more glass cyclocapillary tubes 5 also oriented vertically.

Figure 2:
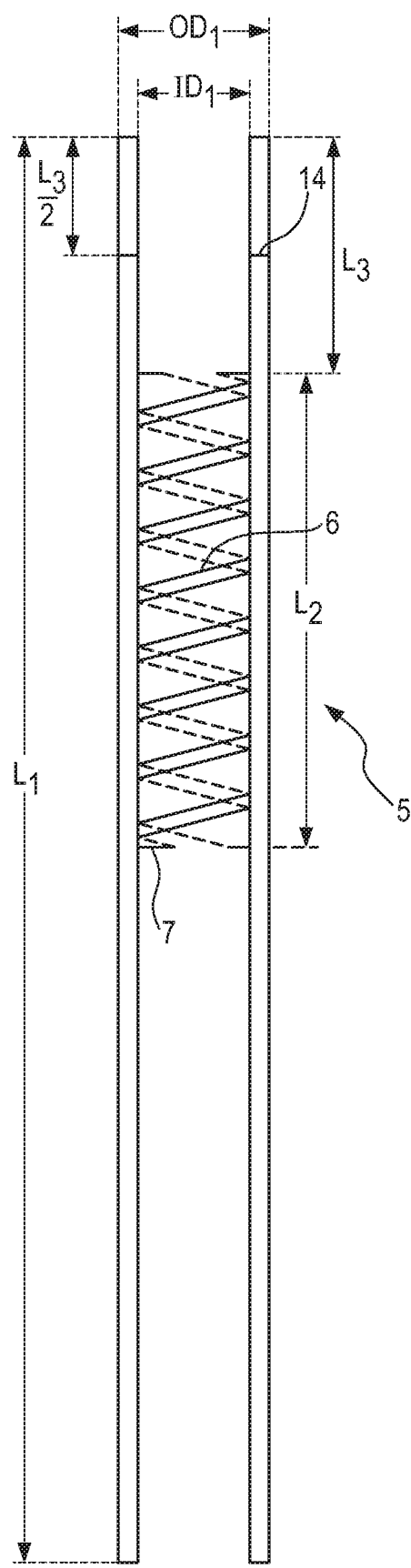
FIG. 2 represents a glass cyclocapillary tube used to measure the burst resistance pressure.

Referring to FIG. 2, a glass cyclocapillary tube 5 is represented. The glass cyclocapillary tubes 5 have a length $L_1$ of 78.5 mm long along the axis of the glass cyclocapillary tube, an outer diameter $OD_1$ of 6.3 mm, and an inner diameter $ID_1$ of 4.0 mm. An internal helical glass cyclocapillary 6 having an inner diameter of 900 m is fixed to the inner wall of the glass cyclocapillary tube toward one end of the tube. The cyclochannel of the internal helical glass cyclocapillary 6 contains 8 turns, has a length $L_2$ of 25.4 mm along the axis of the glass cyclocapillary tube, and is positioned a length $L_3$ of 10.0 mm from the end of the glass cyclocapillary tube. An internal wall 7 is located in the glass cyclocapillary tube such that the only fluid connectivity from one of the glass cyclocapillary tube to the other is through the internal helical glass cyclocapillary. Appropriate glass cyclocapillary tubes are Restek 12074-707 (Restek Corp., Bellefonte, Pa., USA), or equivalent. The connection between the glass cyclocapillary tube(s) 5 and base 4 are fluid tight and are most conveniently removable (such as through a threaded O-ring connection) so that glass cyclocapillary tube(s) 5 can be easily replaced. If more than one glass cyclocapillary tube 5 is present, all tubes are aligned vertically such that the tops of the internal helical glass cyclocapillaries 6 present in each tube are aligned to be within 1 mm of each other vertically.

The apparatus is further configured such that pressurized nitrogen can be applied to the base. A compressed nitrogen source 8 is connected to a pressure regulator 10 and gauge 9 that measures the output pressure of the nitrogen regulator. A suitable pressure gauge has a range of 0 to 145 pounds per square inch (psi) and an accuracy of equal to or better than ±1% full scale (such as catalog number 1287N1, available from McMaster-Carr Supply Company, Elmhurst, Ill., USA, or equivalent). The output 11 of the nitrogen regulator 10 is attached to a coupler 12 capable of making a gas-tight connection with the top of the main tube 3. It is through the connection made by coupler 12 to the main tube 3 that the reservoir 2 and glass cyclocapillary tube(s) 5 are pressured.

Sample Preparation

In the case that finished, packaged composition is sampled, each specimen analyzed is collected from the top 0.8 cm of a freshly opened package using a 6-mm-diameter transfer tube (such as 190195P Spectrum Laboratories Inc., Irving, Tex., USA, or equivalent). Otherwise, composition is sampled with the same transfer tube from a freshly opened vessel in which the composition has been allowed to equilibrate to lab temperature. In either case, a specimen plug of sample composition in the transfer tube is pushed into the topmost portion 13 of the glass cyclocapillary tube without allowing the specimen to travel downward more than the distance corresponding to one-half turn in the cyclocapillary helix. Excess sample composition is removed such that the entire specimen plug is located beneath the mark line 14 located halfway between the top of the internal helical glass cyclocapillary and the top of the glass cyclocapillary tube (that is, located a distance $L_3/2$ from the end of the glass cyclocapillary tube).

Burst Resistance Pressure Determination

With the glass cyclocapillary tube 5 attached to the base 4, the main tube 3 is filled with the artificial eccrine sweat mixture to a level that is between 3 mm beneath the mark line 14 and 1 mm above the mark line 14 (If necessary, the apparatus is inverted momentarily to eliminate any trapped air bubbles). This creates a small positive hydrostatic pressure at the bottom of the specimen plug of composition to ensure interaction of the artificial eccrine sweat mixture. The main tube 3 is plugged (for example with a rubber stopper) to prevent evaporation. One drop of the sweat mixture is then finally added to the top of sample plug of composition in each glass cyclocapillary tube. Each glass cyclocapillary tube present is covered loosely with a small watch glass or inverted centrifuge tubes (such as CLS3213, Sigma Aldrich, St. Louis, Mo., USA, or equivalent). The artificial eccrine sweat and sample composition are allowed to interact in this state for 4.0±0.25 hours.

After 4 hours have passed, the output 11 of the nitrogen regulator 10 is attached with a gas-tight seal (such as a stopper or O-ring coupler) to the reservoir opening 15. The output pressure of the nitrogen regulator is initially set to 0 psi (closed) and is subsequently increased at a rate of $2.9 \times 10^{-2}$ psi/second (1.0 kilopascal/5 seconds). The pressure at which a plug of sample composition visibly fails (that is, either partially or fully displaced from its initial position) is recorded as the burst resistance pressure of an individual specimen plug. (Specimen replicates can be performed in series on apparatus containing a single glass cyclocapillary tube 5 and/or on apparatus containing multiple glass cyclocapillary tubes 5 installed in parallel on base 4 to allow multiple simultaneous analyses on the same overall apparatus. In the case of analysis of multiple specimens in parallel, glass cyclocapillary tubes are plugged with a stopper immediately after specimen failure so as to minimally effect the pressure to failure of any other specimen).

For any sample composition, four like specimens are prepared analyzed, and the arithmetic mean of their individual specimen burst resistance pressures is calculated and reported as the burst resistance pressure in units of psi to the nearest 0.14 psi ($1.0 \times 10^{-2}$ Bar).

Water Vapor Transmission Rate (WVTR) Test Method

The Water Vapor Transmission Rate (WVTR) Test Method is used to measure the water vapor transmission through a skin mimic material to which composition or raw material has been applied relative to that same skin mimic material with no composition or raw material applied. A percent reduction in WVTR is reported.

Laboratory and Controlled-Environment Chamber

The laboratory is maintained at 22±2° C. and 40±20 percent relative humidity (% RH), and all samples and materials are equilibrated to the laboratory conditions for at least 24 hours prior to performing this method. The WVTR Test Method makes use of a controlled-environment chamber that can be controlled to 32±2° C. and 7±3% RH. One suitable instrument is the ProUmid SPSx Vapor Sorption Analyzer (ProUmid GmbH & Co. KG, Ulm, Germany) or equivalent. This particular instrument also includes integrated mass determination of multiple samples and may be convenient for automating portions of this method. The controlled-environment chamber is maintained at this setpoint for the entirety of this method. All steps of the method are assumed to occur in the laboratory environment unless explicitly stated that they take place in the controlled-environment chamber.

Skin Mimic Preparation

The skin mimic material used in this method is VITRO-SKIN® N-19 (IMS Testing Group, Portland, Me., USA) or equivalent. A composition or raw material to be tested is spread uniformly (such as by spreading with a nitrile gloved finger) at a basis weight of 37.5±1.0 grams per square meter (gsm) on a sheet of skin mimic after which circular discs 18 mm in diameter are cut. For any composition or raw material to be test, three replicate 18-mm discs of skin mimic with composition or raw material applied are prepared. Three replicate blank samples (skin mimic with no composition or raw material applied) are also prepared to serve as a "blank" reference.

Figure 3:
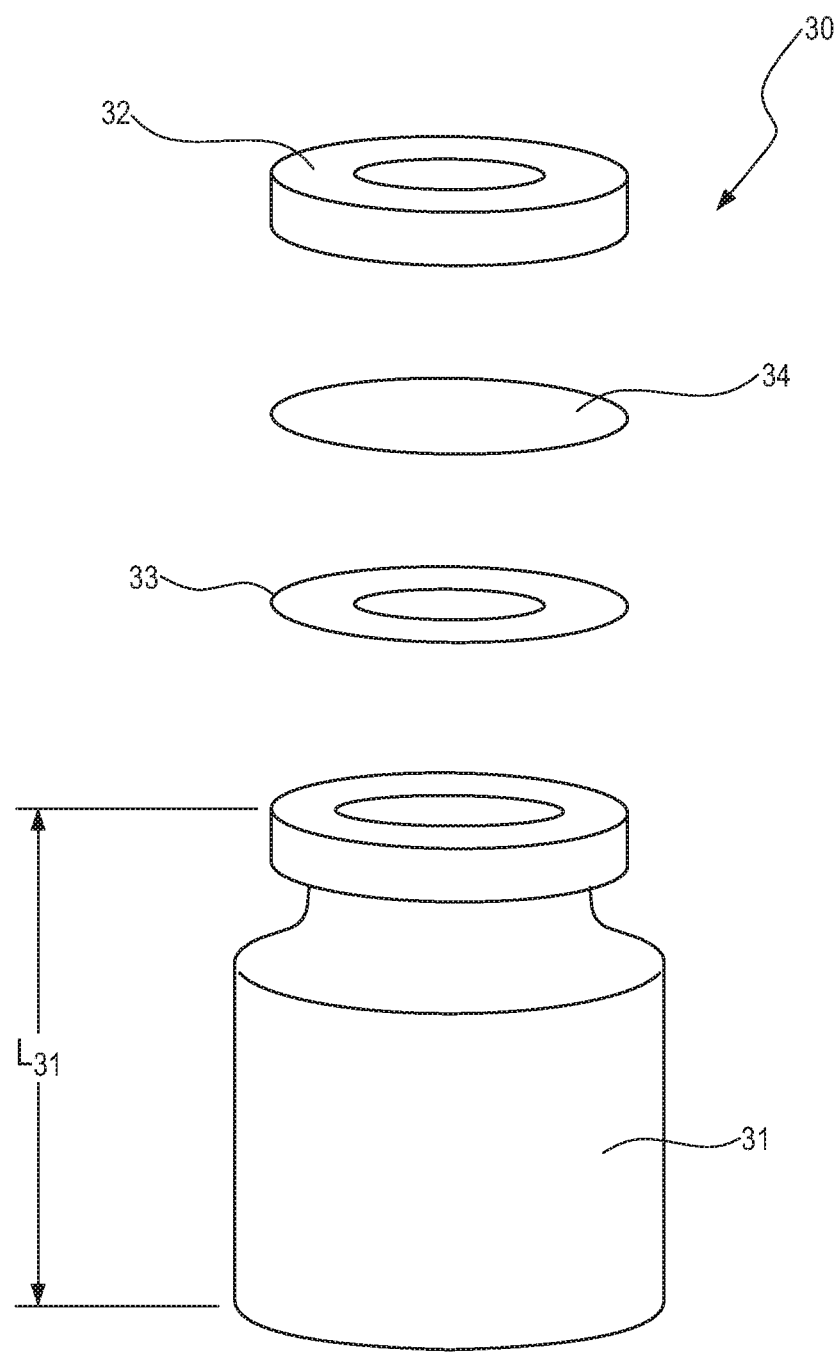
FIG. 3 represents Payne cup measurements to facilitate Water Vapor Transmission Rate (WVTR) measurements of the Water Vapor Transmission Rate Test Method.

Payne cup assemblies Referring to FIG. 3, Payne cup assemblies 30 to facilitate WVTR measurement are constructed from glass serum vials, septum-seal liners, and metal crimp seals. The glass serum vials 31 used are purchased as 5 mL in volume (Wheaton part number 223685, Wheaton Industries, Millville, N.J., USA, or equivalent) and are modified using glassblowing techniques by removing a ring along the parallel cylindrical portion of the wall such that their finished overall length $L_{31}$ is 17±2 mm along the longitudinal axis of the glass serum vial 31. The metal crimp seals 32 and septum-seal liners (PTFE/butyl) used are Wheaton part number 20-0030AS from (Wheaton Industries, Millville, N.J., USA) or equivalent. Prior to use, the septum seals 33 are modified by punching a circular hole 12.4-mm in diameter through the center to create an annulus.

Payne Cup Preparation and Measurement Procedure

For each replicate to be analyzed, the overall Payne cup assembly 30 consists of a glass serum vial 31, an annular septum seal 33, an 18-mm disc of skin mimic 34 (which, for any replicate except a blank replicate have a film of composition or raw material applied as described above), and a crimp seal cap 32. The mass of each Payne cup assembly, defined as the Payne Cup Assembly Mass, is measured in grams (g) to a precision of 0.1 mg or better and is recorded. All subsequent measurements corresponding to a Payne cup after the introduction of water and crimping are understood to have its Payne Cup Assembly Mass subtracted.

For each Payne cup assembly, after recording the Payne Cup Assembly Mass, 2.0±0.2 mL deionized water is added to the serum vial. The annular septum seal 33, the skin mimic 34 (with the surface to which composition was applied facing away from the serum vial 31), and the crimp cap 32 are then arranged on the serum vial 31 as shown in FIG. 3, and the crimp cap is crimped to seal the vial, and the Payne cup is placed in the controlled-environment chamber held at 32±2° C. and 7±3% RH. This is defined as time zero. The Payne cup is removed momentarily from the chamber at 18 hours±10 minutes, and its mass is measured in grams to a precision of 0.1 mg or better and recorded as the Mass at 18 Hours. The Payne cup is finally removed momentarily from the chamber at 24 hours±10 minutes, and its mass is measured in grams to a precision of 0.1 mg or better and recorded as the Mass at 24 Hours. (If using a controlled-environment chamber with in-chamber weighing capabilities, these mass measurements may be conducted within the chamber without Payne cup removal)

Calculations and Reporting

For each Payne cup measured, Payne cup WVTR is calculated using the formula $$WVTR = \frac{\text{Mass at 18 hours (g)} - \text{Mass at 24 hours (g)}}{24 \text{ hours} - 18 \text{ hours}} \times \frac{1}{\pi(6.2 \times 10^{-3} \text{ m})^2}$$

and is recorded in units of grams per square meter per hour (gsm/h) to the nearest 0.1 gsm/h.

For each sample composition or raw material analyzed in triplicate across three prepared Payne cups, the WVTR of the sample, $WVTR_{sample}$, is defined as the average (arithmetic mean) of the three WVTR values of the three individual sample Payne cups measured in triplicate. Similarly, the WVTR of the blank, $WVTR_{blank}$, is defined as the average (arithmetic mean) of the three WVTR values of the three individual blank Payne cups measured in triplicate.

For each sample composition or raw material analyzed, the Percent WVTR Reduction, $\% WVTR_{red}$, can be defined as $$\% WVTR_{red} = 100\% \times \left(1 - \frac{WVTR_{sample}}{WVTR_{blank}}\right)$$

and is reported to the nearest 0.1%.

Water Vapor Sorption Test Method

The Water Vapor Sorption Test Method is used to determine the amount of water vapor sorption that occurs in a raw material or composition between being conditioned with a first environmental state and a second environmental state at elevated temperature and humidity. In this method, product is spread thinly on an inert substrate, and the mass change associated with being conditioned with differing environmental states is captured in a dynamic vapor sorption instrument. The resulting mass gain, expressed as a mass gain per 100 g of composition or raw material, is reported.

This method makes use of a SPSx Vapor Sorption Analyzer with 1 µg resolution (ProUmid GmbH & Co. KG, Ulm, Germany), or equivalent dynamic vapor sorption (DVS) instrument capable of controlling percent relative humidity (% RH) to within ±3%, temperature to within ±2° C., and measuring mass to a precision of ±0.01 mg. The laboratory environment is maintained at 22±2° C. and 40±20% RH, and all samples and materials are equilibrated to the laboratory conditions for at least 24 hours prior to performing this method. Formulations that have been fully packed are equilibrated in their unused, unopened state. Raw materials or experimental formulations that may not have been fully packed are equilibrated to the laboratory environment in a sealed glass jar with a headspace volume representing no greater than 25% of the overall jar volume.

Samples are prepared in the laboratory environment described above. A 20.0±2.0 mg specimen of raw material or composition is spread evenly on a circular (18 mm diameter) disc made of polytetrafluoroethane (PTFE) 50±5 µm (0.002 inches) in thickness. (The disc of PTFE is tared beforehand along with an aluminum sample pan appropriate for the DVS instrument. In this method, all mass measurements presume the subtraction of the mass of the PTFE and sample pan).

The PTFE disc on which raw material or composition specimen has been spread is placed in the DVS instrument with the DVS instrument set to 22° C. and 30% RH at which point an initial mass of the specimen is immediately recorded to a precision of 0.01 mg or better. This is defined as $m_1$. After the specimen is in the DVS for a duration of 48 hours at this environmental setting, the mass $m_2$ of the specimen is recorded to a precision of 0.01 mg or better. The DVS is then set to 32° C. and 70% RH, and the specimen remains in the DVS for a duration of 48 hours at this environmental setting with mass being measured and recorded every 15 minutes to a precision of 0.01 mg or better. The maximum mass measured during this latter 48-hour hold is defined as mass $m_3$.

For a particular specimen, the Water Vapor Sorption Per 100 Grams is defined as $$\text{Water Vapor Sorption Per 100 Grams} = \frac{m_3 - m_2}{m_1} \times 100\,g$$

The Water Vapor Sorption Per 100 Grams is reported in units of grams to the nearest 0.1 g.

Weight Average Particle Size Test Method

The Weight Average Particle Size Test Method is used to determine a characteristic mean particle size of a dry particulate material using laser diffraction. The dry particulate material is a polyquaternium which can be selected from the group consisting of polyquatemium-7, polyquaternium-6, polyquatemium-5, polyquaternium-4, polyquaternium-10, polyquaternium-11, polyquaternium-16, polyquaternium-22, polyquaternium-29, polyquaternium-39, polyquatemium-44, polyquaternium-46, and combinations thereof. Preferred, polyquaternium may be selected from the group consisting of polyquaternium-6, polyquatemium-5, polyquatemium-10, and combinations thereof.

The laboratory environment is maintained at 20±2° C. and 40±20 percent relative humidity (% RH).

A specimen of dry particulate material is first sieved (ASTM E11-17 No. 35 standard sieve, a wire cloth with 500 µm orifice size) using standard mechanical sieving techniques known to those of skill in the art, and any portion of the particulate specimen that is retained by the sieve (that is, has particle size greater than 500 m) is discarded and not further analyzed.

The remaining portion of the particulate specimen is analyzed using a laser-diffraction-based particle size analyzer (Cilas 1190, Cilas, Oleans, France, or equivalent). The laser used is 830 nm in wavelength and has a power of 2 mW. A vibratory feeder is used to feed into a Venturi through which pressurized air delivers the particulate specimen to the portion of the analyzer in which the particles partially obscure the laser beam. The level of obscuration of the particulate specimen in the laser beam is between 1% and 5%, and the duration of the laser scattering and data collection is 15 seconds. A Fraunhofer diffraction model is used, and the volume-weighted mean diameter, $\overline{D}_{4,3}$, is recorded. The arithmetic mean of the determined $\overline{D}_{4,3}$ for three like specimens is calculated and reported as the Weight Average Particle Size in units of micrometers (µm) to the nearest m.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

The following commercial product, Schmidt's Bergamot+Lime natural deodorant stick is free of aluminum-based antiperspirant actives. The Schmidt's Bergamot+Lime natural deodorant stick is available via the Database GNPD [Online] Mintel; August 2018 (2018-08) "Bergamot+Lime natural deodorant stick", Database accession no. 5918775: https://www.gnpd.com/sinatra/recordpage/5918775/.

The Schmidt's Bergamot+Lime natural deodorant stick has the following ingredients: *Maranta arundinacea* (arrowroot) powder, sodium bicarbonate (baking soda), *Cocos nucifera* (coconut) oil, *Butyrospermum parkii* (shea butter), caprylic/capric triglyceride (fractionated coconut oil), *Euphorbia cerifera* (candelilla) wax, *Simmondsia chinensis* (jojoba) seed oil, *Citrus bergamia* (bergamot) essential oil, *Citrus aurantifolia* (lime) essential oil, tocopherol (vitamin E, sunflower derived).

The Schmidt's Bergamot+Lime natural deodorant stick has been assessed in terms of burst resistance pressure, percent water vapor transmission rate reduction, water vapor sorption according to the respective test methods as set out above.

The Schmidt's Bergamot+Lime natural deodorant stick that has been tested was a 92 g (3.25 oz) bar, with a bar code number of 0 19962 08501 7 and a batch number of BL31217.

| Composition (% wt.) | |
|---|---|
| Components | Schmidt's deodorant |
| *Maranta arundinacea* (arrowroot) powder, sodium bicarbonate (baking soda), *Cocos nucifera* (coconut) oil, *Butyrospermum parkii* (shea butter), caprylic/capric triglyceride (fractionated coconut oil), *Euphorbia cerifera* (candelilla) wax, *Simmondsia chinensis* (jojoba) seed oil, *Citrus bergamia* (bergamot) essential oil, *Citrus aurantifolia* (lime) essential oil, tocopherol (vitamin E, sunflower derived) | |
| Burst Resistance Pressure (psi) | 0.8 |
| % $WVTR_{red}$ (%) | 35.4 |
| Water Vapor Sorption per 100 g of the composition (g) | 1.45 |

The Schmidt's Bergamot+Lime natural deodorant stick does not fall within the scope of the present invention because the composition has a burst pressure below 2 psi and has a water vapor sorption below 2.0 g per 100 g of the composition.

The following compositions were prepared. The burst resistance pressure, the percent water vapor transmission rate reduction (% $WVTR_{red}$), and the amount of water vapor sorption per 100 g of the composition were measured for each example according to the respective test methods as set out above.

| | Compositions (% wt.) | | | | |
|---|---|---|---|---|---|
| | Components | Comp. Ex. 1 | Ex. 1 | Ex. 2 | Ex. 3 |
| | Sodium Polyacrylate Starch*[1] | 5 | 5 | 5 | 5 |
| | Tapioca Starch*[2] | 14 | 14 | 14 | 14 |
| Group 2 | Chitosan*[3] | — | 2 | — | — |
| | Polyvinylpyrrolidone*[4] | — | — | 2 | — |
| | Sodium hyaluronate*[5] | — | — | — | 2 |
| Group 1 | 10 Centistoke (cS) Dimethicone*[6] | 37.25 | 35.25 | 35.25 | 35.25 |
| | Mineral oil*[7] | 8 | 8 | 8 | 8 |
| | PEG-12 Dimethicone*[8] | 0.8 | 0.8 | 0.8 | 0.8 |
| | Stearyl alcohol*[9] | 16 | 16 | 16 | 16 |
| | Behenyl alcohol*[10] | 0.2 | 0.2 | 0.2 | 0.2 |
| | Ozokerite wax*[11] | 3 | 3 | 3 | 3 |
| | Petrolatum*[12] | 4 | 4 | 4 | 4 |
| | Sucrose distearate*[13] | 4 | 4 | 4 | 4 |
| | Talc*[14] | 5 | 5 | 5 | 5 |
| | Zinc citrate dihydrate*[15] | 1 | 1 | 1 | 1 |
| | Fragrance | 1.75 | 1.75 | 1.75 | 1.75 |
| Total | | 100 | 100 | 100 | 100 |

-continued

| Components | Comp. Ex. 1 | Ex. 1 | Ex. 2 | Ex. 3 |
|---|---|---|---|---|
| Burst Resistance Pressure (psi) | 1.7 | 3.4 | 2.1 | 2.3 |
| % WVTR$_{red}$ (%) | 43.0 | 47.0 | 41.9 | 40.6 |
| Water Vapor Sorption per 100 g of the composition (g) | 3.3 | 3.4 | 3.6 | 3.5 |

Definitions of Components
*[1]Makimousse 7 available from Kobo, Inc.
*[2]Tapioca Pure available from Akzo Nobel
*[3]Chitoclear ® 42000 - cg10 available from Primex, Iceland: Chitosan having a viscosity of 8 cps, a weight average molecular weight of 42 000, and a degree of deacetylation of 81%
*[4]Polyvinylpyrrolidone (K30 type) available from Ashland Chemical
*[5]Bio-Sodium Hyaluronate Powder available from Biolan
*[6]Xiameter ® PMX-200 Silicone Fluid 10 cS available from Dow Corning
*[7]Benol White Mineral Oil available from Sonnerborn LLC
*[8]Xiameter ® OFX-0193 available from Dow Corning
*[9]CO-1897 Stearyl Alcohol NF Pastilles available from Cremer
*[10]Lanette 22 available from BASF
*[11]Ozokerite wax SP-1026 Type available from Strahk & Pitsch LLC
*[12]Super White Protoper Petrolatum available from Sonnerborn LLC
*[13]Crodesta F110-PW-(JP) available from Croda
*[14]Imperial 250 USP available from Imerys Talc America, Inc.
*[15]Zinc Citrate Dihydrate USP available from Joist Chemical Co.

Comp. Ex. 1 only comprises as the first water-absorbing component, a superabsorbent polymer being sodium polyacrylate starch. Comp. Ex. 1 does not fall within the scope of the present invention because the burst resistance pressure is below 2 psi. However, Comp. Ex. 1 exhibits a better burst pressure and water vapor sorption than the Schmidt's Bergamot+Lime natural deodorant stick.

Ex. 1 additionally comprises a second water-absorbing component being chitosan. When a second water-absorbing component such as chitosan is combined with a superabsorbent polymer like sodium polyacrylate starch, the burst resistance pressure of the anhydrous cosmetic composition is significantly increased while maintaining the water vapor sorption per 100 g of composition. The anhydrous cosmetic composition can help to control dryness at the axillary (underarm) skin, by absorbing and/or adsorbing the released wetness generated from the axillary (underarm) skin by the anhydrous cosmetic composition. Ex. 1 has a better burst resistance pressure and water vapor sorption that the Schmidt's Bergamot+Lime natural deodorant stick. Hence, Ex. 1 can better help to control dryness at the axillary skin than the Schmidt's Bergamot+Lime natural deodorant stick by better providing an efficient spreading, wetting and adhesive film onto the axillary skin surface. Such film onto the axillary skin surface can help prevent or slow down the potential for sweat and transepidermal water to emerge on top of the product and axillary skin surface. The emerging sweat and transepidermal water are better spread over and absorbed and/or adsorbed by the anhydrous cosmetic composition forming a film onto the axillary skin surface. Also, the anhydrous cosmetic composition can better effectively cover the axillary skin surface, spread and adsorb and/or absorb the emerging sweat and transepidermal water generated from the axillary (underarm) skin.

Not only chitosan as a second water-absorbing component can provide such properties, also other second water-absorbing components can show such similar improvements like polyvinylpyrrolidone (Ex. 2) and sodium hyaluronate (Ex. 3) in terms of increased of burst resistance pressure, increased amount of water vapor sorption per 100 g of composition and satisfactory percent water vapor transmission rate reduction (% WVTR$_{red}$).

The following compositions were made:

| | Components | Comp. Ex. 1 | Ex. 4 | Ex. 5 | Ex. 6 | Ex. 7 |
|---|---|---|---|---|---|---|
| | Sodium Polyacrylate Starch*[1] | 5 | 5 | 5 | 5 | 5 |
| | Polyquaternium-6*[16] | — | 2 | 2 | 2 | 2 |
| | Tapioca Starch*[2] | 14 | 14 | 14 | 14 | 14 |
| Group 2 | Chitosan*[3] | — | — | 2 | — | — |
| | Carboxy methyl cellulose*[17] | — | — | — | 2 | — |
| | Sodium hyaluronate*[5] | — | — | — | — | 2 |
| Group 1 | 10 Centistoke (cS) Dimethicone*[6] | 37.25 | 35.25 | 33.25 | 33.25 | 33.25 |
| | Mineral oil*[7] | 8 | 8 | 8 | 8 | 8 |
| | PEG-12 Dimethicone*[8] | 0.8 | 0.8 | 0.8 | 0.8 | 0.8 |
| | Stearyl alcohol*[9] | 16 | 16 | 16 | 16 | 16 |
| | Behenyl alcohol*[10] | 0.2 | 0.2 | 0.2 | 0.2 | 0.2 |
| | Ozokerite wax*[11] | 3 | 3 | 3 | 3 | 3 |
| | Petrolatum*[12] | 4 | 4 | 4 | 4 | 4 |
| | Sucrose distearate*[13] | 4 | 4 | 4 | 4 | 4 |
| | Talc*[14] | 5 | 5 | 5 | 5 | 5 |
| | Zinc citrate dihydrate*[15] | 1 | 1 | 1 | 1 | 1 |
| | Fragrance | 1.75 | 1.75 | 1.75 | 1.75 | 1.75 |
| | Total | 100 | 100 | 100 | 100 | 100 |
| | Burst Resistance Pressure (psi) | 1.7 | 2.8 | 4.5 | 2.8 | 2.9 |
| | Water Vapor Sorption per 100 g of the composition (g) | 3.3 | 3.6 | 4.3 | 5.4 | 4.5 |

Definitions of Components
*[16]Rheosol Q6P available from Rheolab
*[17]Sodium Carboxymethyl Cellulose with a weight average molecular weight of 90 000 available from Milipore Sigma;

Comp. Ex. 1 only comprises as the first water-absorbing component, a superabsorbent polymer being sodium polyacrylate starch. Ex. 4 additionally comprises a polyquaternium like polyquaternium-6. When a polyquaternium like polyquaternium-6 is combined with a superabsorbent polymer like sodium polyacrylate starch, the burst resistance pressure of the anhydrous cosmetic composition is significantly increased while the amount of water vapor sorption per 100 g of composition remains satisfactory. The anhydrous cosmetic composition can help to control dryness at the axillary (underarm) skin, by absorbing the released wetness generated from the axillary (underarm) skin (namely the emerging sweat and transepidermal water generated from the axillary skin) by the anhydrous cosmetic composition.

Such film onto the axillary skin surface can help prevent or slow down the potential for sweat and transepidermal water to emerge on top of the product and axillary skin surface. The emerging sweat and transepidermal water are better spread over and absorbed and/or adsorbed by the anhydrous cosmetic composition forming a film onto the axillary skin surface. Also, the anhydrous cosmetic composition can better effectively cover the axillary skin surface, spread and adsorb and/or absorb the emerging sweat and transepidermal water generated from the axillary (underarm) skin.

When a second water-absorbing component such as chitosan is added to the first water-absorbing component being the mixture of a polyquaternium and a superabsorbent polymer, as shown in Ex. 5, the burst resistance pressure and the amount of water vapor sorption per 100 g of composition have been further increased. Ex. 5 can even more control dryness at the axillary (underarm) skin, by absorbing even more the released wetness generated from the axillary (underarm) skin by the anhydrous cosmetic composition. Such film onto the axillary skin surface can help further for preventing or slowing down the potential for sweat and transepidermal water to emerge on top of the product and axillary skin surface. The emerging sweat and transepidermal water are better spread over and absorbed and/or adsorbed by the anhydrous cosmetic composition forming a film onto the axillary skin surface. Also, the emerging sweat and transepidermal water generated from the axillary (underarm) skin can be even more covered at the axillary skin surface, spread and adsorbed and/or absorbed by the anhydrous cosmetic composition.

Not only chitosan as the second water-absorbing component can provide such properties, also other second water-absorbing components can show such similar improvements like carboxy methyl cellulose (Ex. 6) and sodium hyaluronate (Ex. 7) in terms of increased amount of water vapor sorption per 100 g of composition.

The following compositions were made:

| | | Compositions (% wt.) | | | | |
|---|---|---|---|---|---|---|
| | Components | Comp. Ex. 1 | Ex. 4 | Ex. 8 | Ex. 9 | Ex. 10 |
| Group 1 | Sodium Polyacrylate Starch*[1] | 5 | 5 | 5 | 5 | 5 |
| | Polyquaternium-6*[16] | — | 2 | 2 | — | — |
| | Polyquaternium-5*[18] | — | — | — | 2 | — |
| | Polyquaternium-10*[19] | — | — | — | — | 2 |
| | Tapioca Starch*[2] | 14 | 14 | — | — | — |
| | 10 Centistoke (cS) Dimethicone*[6] | 37.25 | 35.25 | 49.25 | 49.25 | 49.25 |
| | Mineral oil*[7] | 8 | 8 | 8 | 8 | 8 |
| | PEG-12 Dimethicone*[8] | 0.8 | 0.8 | 0.8 | 0.8 | 0.8 |
| | Stearyl alcohol*[9] | 16 | 16 | 16 | 16 | 16 |
| | Behenyl alcohol*[10] | 0.2 | 0.2 | 0.2 | 0.2 | 0.2 |
| | Ozokerite wax*[11] | 3 | 3 | 3 | 3 | 3 |
| | Petrolatum*[12] | 4 | 4 | 4 | 4 | 4 |
| | Sucrose distearate*[13] | 4 | 4 | 4 | 4 | 4 |
| | Talc*[14] | 5 | 5 | 5 | 5 | 5 |
| | Zinc citrate dihydrate*[15] | 1 | 1 | 1 | 1 | 1 |
| | Fragrance | 1.75 | 1.75 | 1.75 | 1.75 | 1.75 |
| Total | | 100 | 100 | 100 | 100 | 100 |
| Burst Resistance Pressure (psi) | | 1.7 | 2.8 | 2.1 | 2.2 | 3.1 |
| Water Vapor Sorption per 100 g of the composition (g) | | 3.3 | 3.6 | 2.1 | 2.1 | 2.6 |

Definitions of Components
*[18]Merquat 5 available from Lubrizol
*[19]Conditioner P10 available from 3V Sigma Now, it has been shown, that the effect of combining a polyquaternium with a superabsorbent polymer on the increased burst resistance pressure is not limited to polyquaternium-6 with or without Tapioca starch (Ex. 4 and Ex. 8). The effect of combining a polyquaternium with a superabsorbent polymer on the increased burst resistance pressure is also observed when replacing polyquaternium-6 with polyquaternium-5 (Ex. 9) or polyquaternium-10 (Ex. 10). Water vapor sorption values remain satisfactory.

Method of Preparation

The above anhydrous cosmetic compositions of "Ex. 1" through "Ex. 10" and "CEx. 1" were prepared by the following method:

Group 1 components were mixed and heated at 88° C. until a relatively clear uniform melted mixture is obtained in an overhead mixer. The overall mixture was cooled between 70° C. and 78° C. Then, sucrose distearate, sodium hyaluronate when applicable, and then talc were added to the previous mixture. Then, the respective polyquaternium when applicable is added followed by Group 2 components when applicable. Zinc citrate dihydrate is subsequently added and the temperature is dropped to 70° C. Tapioca Starch when applicable was added following with the super-absorbent polymer, i.e. sodium polyacrylate starch when applicable. The mixture was milled at 13,000 rpm until a uniform mixture was obtained before adding the fragrance. Finally, the obtained mixture was cooled to 58° C., then is poured into an appropriate container, and allowed to cool and solidify.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An anhydrous cosmetic stick composition, or an anhydrous deodorant stick composition, comprising:
    (a) only one absorbing component, consisting of starch particles selected from the group consisting of tapioca starch, corn starch, potato starch, glyceryl starch, calcium starch octenyl succinate, polymethylsilsesquioxane coated tapioca starch, and arrowroot starch;
    (b) a malodour-controlling component;
    (c) a cosmetically acceptable carrier comprising two or more structurants;
    wherein the anhydrous cosmetic composition has a burst resistance pressure greater than about 137.9 mBar (2 psi) as measured according to the Burst Resistance Pressure Test Method as disclosed herein;
    wherein the anhydrous cosmetic composition has a water vapor sorption per 100 g of the composition from about 2.0 g to about 15 g as measured according to the Water Vapor Sorption Test Method as disclosed herein; and
    wherein the anhydrous cosmetic composition is essentially free of aluminium-based antiperspirant actives.

2. The anhydrous cosmetic composition of claim 1, wherein the anhydrous cosmetic composition has a percent water vapor transmission rate reduction from about 20% to about 50% as measured according to the Water Vapor Transmission Rate Test Method as disclosed herein.

3. The anhydrous cosmetic composition of claim 1, wherein the one absorbing component has
    a water vapor sorption from about 2.0 g to about 8.4 g per 100 g of itself according to the Water Vapor Sorption Test Method as disclosed herein.

4. The anhydrous cosmetic composition of claim 1, wherein the malodour-controlling component is selected from the group of piroctone olamine, zinc oxide, zinc citrate, zinc citrate dihydrate, zinc carbonate, zinc hydroxide, zinc lactate, zinc gluconate, zinc ricinoleate, decylene glycol, salicylic acid, citric acid, dehydroacetic acid and mixtures thereof.

5. The anhydrous cosmetic composition of claim 1, wherein the composition does not comprise any aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, aluminum zirconium trichlorohydrex gly, aluminum hydrochloride, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol as antiperspirant active component.

6. The anhydrous cosmetic composition of claim 1, wherein the anhydrous cosmetic composition is a deodorant.

7. The anhydrous cosmetic composition of claim 1, wherein the anhydrous cosmetic composition is an antimicrobial composition.

* * * * *